(12) United States Patent
Bley et al.

(10) Patent No.: US 9,024,055 B2
(45) Date of Patent: May 5, 2015

(54) ACETAMINOPHEN CONJUGATES, COMPOSITIONS AND METHODS OF USE THEREOF

(71) Applicant: Acorda Therapeutics, Inc., Ardsley, NY (US)

(72) Inventors: Keith R. Bley, Menlo Park, CA (US); Bernd Jandeleit, Menlo Park, CA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

(21) Appl. No.: 14/346,689

(22) PCT Filed: Sep. 21, 2012

(86) PCT No.: PCT/US2012/056625
§ 371 (c)(1),
(2) Date: Mar. 21, 2014

(87) PCT Pub. No.: WO2013/044064
PCT Pub. Date: Mar. 28, 2013

(65) Prior Publication Data
US 2014/0243407 A1 Aug. 28, 2014

Related U.S. Application Data

(60) Provisional application No. 61/538,075, filed on Sep. 22, 2011.

(51) Int. Cl.
*C07C 329/06* (2006.01)
*C07C 313/04* (2006.01)

(52) U.S. Cl.
CPC .............. *C07C 329/06* (2013.01); *C07C 313/04* (2013.01)

(58) Field of Classification Search
CPC ............................ C07C 313/04; C07C 329/06
USPC .................... 514/490, 512; 558/248; 560/163
See application file for complete search history.

(56) References Cited

U.S. PATENT DOCUMENTS

| | | | |
|---|---|---|---|
| 4,322,410 A | 3/1982 | Stjepanovic et al. | |
| 5,985,856 A | 11/1999 | Stella et al. | |
| 6,204,257 B1 | 3/2001 | Stella et al. | |
| 6,451,776 B2 | 9/2002 | Stella et al. | |
| 6,872,838 B2 | 3/2005 | Stella et al. | |
| 7,244,718 B2 | 7/2007 | Stella et al. | |
| 8,575,217 B2 * | 11/2013 | Mian et al. | 514/562 |
| 8,735,376 B2 | 5/2014 | Muhammad et al. | |
| 2008/0318905 A1 | 12/2008 | Muhammad et al. | |
| 2010/0234452 A1 | 9/2010 | Mian et al. | |
| 2011/0212926 A1 | 9/2011 | Muhammad et al. | |
| 2011/0263545 A1 | 10/2011 | Muhammad et al. | |
| 2014/0228326 A1 | 8/2014 | Muhammad et al. | |

FOREIGN PATENT DOCUMENTS

| | | |
|---|---|---|
| WO | WO-2009/143295 A1 | 11/2009 |
| WO | WO-2009/143299 A1 | 11/2009 |
| WO | WO-2010/030781 A2 | 3/2010 |
| WO | WO-2010/030781 A3 | 3/2010 |

OTHER PUBLICATIONS

Acharya, M. et al. (Aug. 24, 2010). "Comparison of the Protective Actions of N-Acetylcysteine, Hypotaurine and Taurine Against Acetaminophen-Induced Hepatotoxicity in the Rat," *J. Biomed. Science* 17(Suppl 1):S35.
Bridger, S. et al. (Jun. 6, 1998). "Deaths From Low Dose Paracetamol Poisoning," *BMJ* 316(7146):1724-1725.
Dipiro, J.T. et al. (2005). *Pharmacotherapy: A Pathophysiologic Approach*, 6th edition, McGraw-Hill, pp. 133.
Emoto, C. et al. (Oct. 2010). "Methodologies for Investigating Drug Metabolism at the Early Drug Discovery Stage: Prediction of Hepatic Drug Clearance and P450 Contribution," *Current Drug Metab.* 11(8):678-685.
FDA.GOV (2009). "Acetaminophen Overdose and Liver Injury—Background and Options for Reducing Injury," located at <http://www.fda.gov/downloads/AdvisoryCommitteesMeetingMaterials/Drugs/DrugSafetyandRiskManagementAdvisoryCommittee/UCM164897.pdf>, last visited Nov. 17, 2014, 21 pages.
Hadzimichalis, N.M. et al. (Dec. 2007; e-pub. Oct. 5, 2007). "Acetaminophen-Mediated Cardioprotection Via Inhibition of the Mitochondrial Permeability Transition Pore-Induced Apoptotic Pathway," *Am. J. Physiol. Heart Circ. Physiol.* 293(6):H3348-H3355.
Hardman, J. et al. (Aug. 2001). *Goodman and Gillman's The Pharmacological Basis of Therapeutics*, 10th edition, McGraw-Hill Professional, pp. 704.
Haynes, D.A. et al. (Oct. 2005). "Occurrence of Pharmaceutically Acceptable Anions and Cations in the Cambridge Structural Database," *J. Pharm. Sci.* 94(10):2111-2120.
International Search Report mailed on Dec. 3, 2012 for PCT Application No. PCT/US2012/056625, filed on Sep. 21, 2012, three pages.
Johnson, J.L. et al. (Aug. 2003). "Prediction of Precipitation-Induced Phlebitis: A Statistical Validation of an In Vitro Model," *J. Pharm. Sci.* 92(8):1574-1581.
Lee, W.M. (Jul. 2004). "Acetaminophen and the U.S. Acute Liver Failure Study Group: Lowering the Risks of Hepatic Failure," *Hepatology* 40(1):6-9.
Maharaj, H. et al. (Sep. 2006). "Acetylsalicylic Acid and Acetaminophen Protect Against Oxidative Neurotoxicity," *Metabolic Brain Disease* 21(2-3):180-199.
Moller, P.L. et al. (May 2005; e-pub. Mar. 24, 2005). "Onset of Acetaminophen Analgesia: Comparison of Oral and Intravenous Routes After Third Molar Surgery," *British J. Anaesth.* 94(5):642-648.
Moller, P.L. et al. (Jul. 2005). "Intravenous Acetaminophen (Paracetamol): Comparable Analgesic Efficacy, But Better Local Safety Than Its Prodrug, Propacetamol, for Postoperative Pain After Third Molar Surgery," *Anesth. Analg.* 101(1):90-96.

(Continued)

*Primary Examiner* — Shailendra Kumar
(74) *Attorney, Agent, or Firm* — Morrison & Foerster LLP

(57) ABSTRACT

Acetaminophen conjugates are provided, which have an acetaminophen moiety covalently linked to a second moiety. The conjugates provided may have one or more advantageous properties, including increased water solubility as compared to acetaminophen, reduced toxicity profile as compared to acetaminophen and an altered pharmacokinetic profile. Formulations comprising the conjugates are also provided, as are methods of using the conjugates and kits comprising the conjugates.

9 Claims, 8 Drawing Sheets

(56) References Cited

OTHER PUBLICATIONS

Pasetto, P. et al. (Jun. 22, 2005). "Synthesis and Characterisation of Molecularly Imprinted Catalytic Microgels for Carbonate Hydrolysis," *Analytica Chimica Acta* 542(1):66-75.

Poste, G. et al. (1976). "Lipid Vesicles as Carriers for Introducing Biologically Active Materials Into Cells," Chapter 4 *in Methods in Cell Biology*, vol. XIV, Academic Press, Inc., New York:NY., pp. 33-71.

Sener, G. et al. (Jan.-Feb. 2005). "Protective Effects of MESNA (2-Mercaptoethane Sulphonate) Against Acetaminophen-Induced Hepatorenal Oxidative Damage in Mice," *J. Appl. Toxicol.* 25(1):20-29.

Taniguchi, M. et al. (1981). "Synthesis and Evaluation in Vitro of 4-Acetamidophenyl Phosphate," *Chem. Pharm. Bulletin* 29(2):577-580.

Tripathy, D. et al. (Mar. 16, 2009). "Acetaminophen Inhibits Neuronal Inflammation and Protects Neurons From Oxidative Stress," *J. Neuroinflammation* 6:10.

Watkins, P.B. et al. (Jul. 5, 2006). "Aminotransferase Elevations in Healthy Adults Receiving 4 Grams of Acetaminophen Daily: A Randomized Controlled Trial," *JAMA* 296(1):87-93.

Written Opinion mailed on Dec. 3, 2012 for PCT Application No. PCT/US2012/056625, filed on Sep. 21, 2012, five pages.

* cited by examiner

| PK Parameters: Oral | Unit | Oral Acetaminophen | Oral Test Article B | Oral Test Article A | Oral Test Article C |
|---|---|---|---|---|---|
| $t_{1/2}$ | hr | 1.4 | 3.9 | 2.1 | no value |
| $T_{max}$ | hr | 0.2 | 0.2 | 0.5 | 8.0 |
| $C_{max}$ | ng/mL | 2204 | 417 | 1002 | 283 |
| $AUC_{last}$ | hr·ng/mL | 3313 | 836 | 3737 | 1138 |
| Relative exposure | % | -- | 27.0 | 119.6 | 40.3 |
| %F | % | 65.3 | 92.4 | 56.9 | 158.6 |

Figure 2A

| PK Parameters: IV | Unit | IV Acetaminophen | IV Test Article B | IV Test Article A | IV Test Article C |
|---|---|---|---|---|---|
| $t_{1/2}$ | hr | 1.5 | 5.3 | 1.2 | no value |
| $T_{max}$ | hr | 0.083 | 0.083 | 0.083 | 0.083 |
| $C_{max}$ | ng/mL | 2075 | 424 | 2555 | 240 |
| $AUC_{last}$ | hr*ng/mL | 1466.9 | 267.8 | 1931.5 | 228.6 |
| $Vz_{obs}$ | mL/kg | 0.0052 | 0.0641 | 0.0027 | no value |
| $Cl_{obs}$ | mL/hr/kg | 0.0024 | 0.0109 | 0.0017 | no value |
| $Vss_{obs}$ | mL/kg | 0.0027 | 0.0294 | 0.0014 | no value |
| Relative exposure | % | -- | 18.3 | 131.7 | 85.4 |

Figure 2B

ACETAMINOPHEN CONJUGATES, COMPOSITIONS AND METHODS OF USE THEREOF

CROSS-REFERENCE TO RELATED APPLICATIONS

This patent application is a National Phase application under 35 U.S.C. §371 of International Application No. PCT/US2012/056625, filed Sep. 21, 2012 and claims priority to U.S. Provisional Patent Application No. 61/538,075, filed Sep. 22, 2011, the disclosures of which are hereby incorporated herein by reference in their entirety.

BACKGROUND OF THE INVENTION

Acetaminophen (USAN) or paracetamol (INN) (chemically known as N-(4-hydroxyphenyl)acetamide or N-(4-hydroxyphenyl)ethanamide) is an antipyretic and analgesic commonly used to manage fever of any etiology, minor to severe pains (including post-operative pain) and a variety of aches. Acetaminophen is well tolerated and lacks many of the undesired effects of other analgesics, such as non-steroidal anti-inflammatory drugs (NSAIDs) or types of cyclooxygenase (COX) inhibitors (e.g., stomach lining irritation, adverse effects on platelets and renal function, fetal ductus arterious closure complications, and Reye's syndrome).

Acetaminophen has also been shown to be effective in protecting tissues from ischemic damage (i.e. damage caused by ischemia as well as reperfusion that follows ischemia). For instance, in guinea pigs, acetaminophen was found to decrease apoptosis in myocytes, which were subjected to low-flow global myocardial ischemia for 30 minutes followed by 60 minutes of reperfusion (See *Am J Physiol Heart Circ Physiol* 293: H3348-H3355, 2007). In another study, acetaminophen was found to inhibit both lipid peroxidation and superoxide anion generation, resulting in retained structural integrity of the rat hippocampus insulted with quinolinic acid in a cerebral ischemia model (See *Metabolic Brain Disease* 21 (2-3): 180-190, 2006). Following a study with cultured CNS neurons, it was concluded that acetaminophen has anti-oxidant and anti-inflammatory effects on neurons (See *J Neuroinflammation* 6:10 doi: 10.1186/1742-2094-6-10, 2009). As with its analgesic applications, an important element of the treatment of ischemic or neurological diseases with acetaminophen is the speed at which therapeutic intervention and peak therapeutic blood concentration occurs.

Opioids have gained widespread use in the clinical setting (for example, to control post-operative pain) due to their excellent analgesic properties and onset of action. However, the use of certain opioids is often accompanied by significant adverse side-effects (e.g., respiratory depression, biliary spasm, constipation, sedation, addiction and abuse potential, and post-operative nausea and vomiting, etc.) which make them less desirable. The alternative use of NSAIDs, however, impairs blood clotting (in addition to the side effects previously mentioned), which is highly undesirable in post-operative settings that require active wound healing and blood clotting. Due to the undesirable qualities of certain NSAIDs, COX inhibitors, and opioids, particularly in certain clinical settings, there has been a need to develop effective formulations of acetaminophen and/or alternative therapies to acetaminophen.

However, it is well known that under certain conditions acetaminophen may be toxic to the liver (known as hepatotoxicity). It is estimated that most liver transplants in the United States are caused by acetaminophen toxicity, and 49% of all acute liver failure cases in 2004 were the result of acetaminophen overdose. Each year, overdoses of acetaminophen (sold as Tylenol® and other brands) account for more than 56,000 emergency room visits and an estimated 458 deaths from acute liver failure (Harvard Women's Health Watch, March, 2006). According to a study from the U.S. Acute Liver Failure Study Group (Lee W M. *Hepatology* 2004 40(1):6-9), acetaminophen-related liver failure appears to be on the rise. Researchers at the University of Washington Medical Center in Seattle found that between 1998 and 2003, the percentage of acute liver failure cases attributed to acetaminophen nearly doubled, rising from 28% to 51%. Acetaminophen toxicity may go beyond liver and may involve kidneys and/or myocardium (JT DiPiro, R L Talbert, G C Yee, G R Matzke, B G Wells, L M Posey (eds) Pharmacotherapy: A Physiological Approach $6^{th}$ ed McGraw Hill (New York 2005) pp. 133). For extensive information collected by the US FDA for an Advisory Panel meeting on acetaminophen-related toxicity, see http://www.fda.gov/downloads/AdvisoryCommittees/CommitteesMeetingMaterials/Drugs/Drug SafetyandRiskManagementAdvisoryCommittee/UCM164897.pdf.

Acetaminophen induced hepatic toxicity has been found to be dependent on both acetaminophen blood level concentration and length of exposure. Previously, acetaminophen package labels instructed patients to not use the maximum dosage (4,000 mg per day) for more than 10 days, and to not take the product for pain for more than 10 days, or for fever for more than 3 days unless directed by a physician. Even healthy adults receiving 4,000 mg of acetaminophen per day for 14 days show elevated levels of enzymes indicative of liver toxicity (*Journal Amer. Med. Assoc.* 296, 87-93, 2006). In 2011 the US FDA announced that it is asking manufacturers of prescription acetaminophen combination products to limit the maximum amount of acetaminophen in these products to 325 mg per tablet, capsule, or other dosage unit. FDA believes that limiting the amount of acetaminophen per tablet, capsule, or other dosage unit in prescription products will reduce the risk of severe liver injury from acetaminophen overdosing, an adverse event that can lead to liver failure, liver transplant, and death. In response to these concerns, the pharmaceutical company Johnson and Johnson relabeled its products to recommend a maximum daily dose of no more than 3000 mg per day. Compounds that provide the therapeutic benefit of acetaminophen but which exhibit reduced hepatic toxicity would be particularly beneficial.

Acetaminophen's previous daily dose limit of 4 grams reduces its therapeutic utility, as 4 grams can be consumed in 16 hours (1 gram every 4 hours) leaving the remaining 8 hours of the day to seek alternative analgesics. Further, ethnic and intersubject variability in acetaminophen metabolism have been reported to be as high as 60-fold (S. Bridger, et al. BMJ 1998; 316:1724-1725), which complicates the acetaminophen safety profile as it imparts a high degree of uncertainty in the toxic dose for a given patient. By attenuating toxicity, improved compounds may provide greater utility by allowing doses higher than 4 grams and/or provide a larger safety margin for patients of any ethnic background. For use in patients with neuronal or myocardial injury, which takes advantage of acetaminophen's ability to protect tissues, the ability to administer high dose levels without fear of hepatotoxicity would be particularly attractive to physicians. Hepatoprotectant acetaminophen mutual prodrugs have been described, e.g., in PCT Publication No. WO 2009/143299.

Parenteral formulations of acetaminophen (e.g., intravenous formulations) would be particularly useful in clinical settings. Compared to oral formulations, an acetaminophen parenteral dosage form, such as intravenous bolus or subcutaneous injection, would have various therapeutic advantages. For instance, parenteral acetaminophen may have relatively faster onset of action and ease of administration in settings such as post surgical recovery and trauma. Additionally, as acetaminophen has a relatively short half-life (about 2 hours; see *Goodman and Gillman's The Pharmacological Basis of Therapeutics* 10th ed, McGraw-Hill 2001, p 704), parenterally-administered acetaminophen may be provided at a lower dosage than oral acetaminophen, since much of the orally-administered acetaminophen is cleared from the body through conjugative first pass metabolism in the liver before reaching peak blood concentrations.

Despite a desire for an acetaminophen dosage form suitable for parenteral administration, development of effective therapeutic acetaminophen beyond oral dosage forms has been limited. A major barrier to developing a parenteral dosage form has been acetaminophen's low water solubility (about 1.3 g per 100 mL). To address acetaminophen's inherent solubility, U.S. Pat. No. 4,322,410 discloses, e.g., a water soluble phosphate derivative of acetaminophen (4-acetamidophenyl dihydrogen phosphate), which has a reported water solubility of 50 g per 100 mL of water. However, this acetaminophen derivative is reportedly not readily amenable to chemical and/or enzymatic hydrolysis (and thus not amenable to clinical use) as it requires alkaline phosphatase and about 15 hours in vitro to yield the desired acetaminophen drug from the derivative (see *Chemical and Pharmaceutical Bulletin* 29 (2): 577-580, 1981). Other phosphate-containing prodrugs have been disclosed in, for example, U.S. Pat. Nos. 4,322,410; 5,985,856; 6,204,257; 6,451,776; 6,872,838; and 7,244,718; U.S. patent application Ser. No. 11/999,660 (US2008/0318905), filed Dec. 5, 2007 and PCT Publication No. WO 2009/143295. Additional accetaminophen prodrugs have been described in U.S. Patent Application Publication No. 20110212926, U.S. Patent Application Publication No. 20110212927 and PCT Publication No. WO 2009/143299.

An injectable ester prodrug of acetaminophen with improved solubility profile, Propacetamol® (4-acetamidophenyl 2-(diethylamino)acetate) was developed in Europe and was later shown to have an inferior local tolerance profile when compared to acetaminophen (90% vs. 52%, *British Journal of Anaesthesia* 94 (5): 642-648, 2005; 49% vs. 0%, *Anesthesia and Analgesia* 101; 90-96, 2005). Another acetaminophen product marketed in Europe, Perfalgan®, is a large-volume (100-mL) formulation of acetaminophen for intravenous infusion over a relatively long period (about 15 minutes). These products are not optimal clinical solutions either because of their tolerance profile or administration requirements.

Thus, there is still a clear unmet need for improved acetaminophen type drugs, such as agents which exhibit enhanced water solubility and/or reduced hepatotoxicity as compared to acetaminophen. For use in patients with neuronal or myocardial injury, which takes advantage of acetaminophen's ability to protect tissues, the ability to rapidly and conveniently administer high dose levels would be particularly attractive to health care providers.

The disclosures of all publications, patents, patent applications and other references referred to herein are hereby incorporated herein by reference in their entireties.

BRIEF SUMMARY OF THE INVENTION

One aspect of the present invention provides a compound of the formula (I):

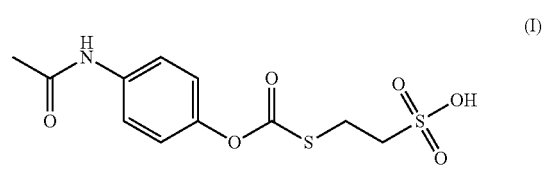 [SMILES: CC(=O)Nc1ccc(OC(=O)SCCS(=O)(=O)O)cc1]

or a pharmaceutically acceptable salt thereof or solvate of the foregoing.

In another aspect a compound of the formula (II) is provided:

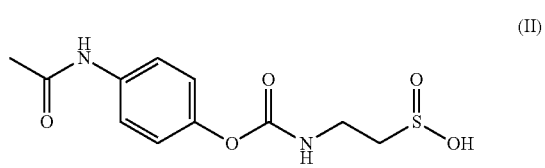 [SMILES: CC(=O)Nc1ccc(OC(=O)NCCS(=O)O)cc1]

or a pharmaceutically acceptable salt thereof or solvate of the foregoing.

In one aspect, a pharmaceutically acceptable salt of a compound of formula (I) or (II) is provided, wherein the salt differs from the parent compound by replacement of an acidic proton present in the parent compound with a metal ion such as sodium.

Also embraced is a formulation comprising: (a) a compound provided herein, such as a compound of formula (I) or (II), or a pharmaceutically acceptable salt thereof or solvate of the foregoing, and (b) a carrier. In some embodiments, the formulation comprises an effective amount of the compound of formula (I) or a pharmaceutically acceptable salt thereof and a carrier. In some of these embodiments, the carrier is a pharmaceutically acceptable carrier, such as a carrier that is amenable to parenteral administration.

In some embodiments, the invention embraces a formulation comprising (a) a compound provided herein, such as a compound of formula (I) or (II), or a pharmaceutically acceptable salt thereof or solvate of the foregoing, and (b) an opioid, a non-steroidal anti-inflammatory drug (NSAID), a benzodiazepine, and/or a barbiturate. In some embodiments, the invention embraces a formulation comprising (a) the compound of formula (I) or (II) or a pharmaceutically acceptable salt thereof or solvate of the foregoing, and (b) codeine, morphine, hydrocodone, hydromorphone, levorphanol, aspirin, ketorolac, ibuprofen, naproxen, caffeine, tramadol, dextropropoxyphene, methylhexital, diazepam, lorazepam, midazolam, propoxyphene, ketoprofen, flurbiprofen, etodolac, diclofenac, misoprostol, meloxicam, piroxicam, doxylamine, pamabrom, carisoprodol, pregabalin, gabapentin, duloxetine and/or butalbital.

In some embodiments, the invention embraces a substantially pure form of a compound provided herein, such as a compound of formula (I) or (II), or a pharmaceutically acceptable salt thereof or solvate of the foregoing.

In another aspect, the present invention provides methods of treating a disease or condition that is responsive to acetaminophen (e.g., pain, fever, inflammation, ischemic injury (such as myocardial and/or cerebral), neuronal injury, etc.) comprising administering to an individual an effective amount of a compound provided herein, such as a compound of formula (I) or (II), or a pharmaceutically acceptable salt thereof or solvate of the foregoing. In some embodiments of the method, the compound is administered parenterally. In some embodiments, the compound is administered intravenously. In some embodiments, the compound is administered intramuscularly. In some embodiments, the compound is administered subcutaneously.

In another aspect, the present invention provides methods of treating a disease or condition that is responsive to acetaminophen (e.g., pain, fever, inflammation, ischemic injury (such as myocardial and/or cerebral), neuronal injury, etc.) comprising administering to an individual a formulation comprising an effective amount of a compound provided herein, such as a compound of formula (I) or (II), or a pharmaceutically acceptable salt thereof or solvate of the foregoing.

In another aspect, methods of providing a more rapid onset of acetaminophen action in an individual are described, the methods comprising administering to the individual an effective amount of a compound of formula (I) or (II), or a pharmaceutically acceptable salt thereof or solvate of the foregoing, wherein the compound provides a more rapid onset of acetaminophen action as compared to a comparable administration of acetaminophen (e.g., from available formulations, which require infusions instead of bolus administrations). A comparable administration of acetaminophen may in one variation be determined to be the amount of acetaminophen required to provide the same dosage amount of acetaminophen in the same dosage form (e.g., I.V. vs. oral) as is provided by the conjugate compound in vivo, where the same dosage amount may in one aspect be assessed by assuming 100% conversion of the conjugate compound to acetaminophen.

In another aspect, the present invention provides a method of providing acetaminophen to an individual, the method comprising administering to the individual an effective amount of a compound of formula (I) or (II), or a pharmaceutically acceptable salt thereof or solvate of the foregoing, wherein the compound, upon administration to the individual, converts to acetaminophen in vivo.

In another aspect, the present invention provides a method of normalizing responsiveness to acetaminophen, the method comprising administering to an individual who is or is suspected of being a member of a population for which administration of acetaminophen provides variable levels of therapeutically accessible acetaminophen in vivo (e.g., by variable levels of glucuronidation and/or sulfation of acetaminophen by the individuals within the population) an effective amount of a compound of formula (I) or (II), or a pharmaceutically acceptable salt thereof or solvate of the foregoing, wherein the compound, upon administration to the individual, converts to acetaminophen in vivo. Variable rates of glucuronidation are increasingly recognized as contributing to variable drug exposure in humans (Emoto C. et al., *Curr Drug Metab.* 2010 11(8):678-85, 2010), and glucuronidation is the primary metabolic fate of acetaminophen. Without being bound by theory, it is believed that the compounds detailed herein, by blocking the sites of acetaminophen glucuronidation and/or sulfation, may result in more predictable and/or normalized exposure to acetaminophen upon administration to an individual as compared to administration of acetaminophen. A method of providing pain relieve to an individual in need thereof is also provided, the method comprising administering to an individual who is or is suspected of being a member of a population for which administration of acetaminophen provides variable levels of therapeutically accessible acetaminophen in vivo an effective amount of a compound of formula (I) or (II), or a pharmaceutically acceptable salt thereof or solvate of the foregoing. Also detailed herein is a method of providing an individual with acetaminophen in vivo, wherein the method comprises administering a compound of formula (I) or (II), or a pharmaceutically acceptable salt thereof or solvate of the foregoing to an individual and wherein the compound is metabolized in vivo to acetaminophen. In one variation, administration of a compound of formula (I) or (II), or a pharmaceutically acceptable salt thereof or solvate of the foregoing results in an altered pharmacokinetic profile of acetaminophen as compared to the pharmacokinetic profile obtained upon administration of acetaminophen. It is understood that pharmacokinetic profiles may be assessed by known methods.

In some embodiments, a compound provided herein, such as a compound of formula (I) or (II), or a pharmaceutically acceptable salt thereof or solvate of the foregoing is administered to an individual in a dosage that provides in vivo the recommended dosage of acetaminophen to an individual. It is understood that compounds provided herein, such as a compound of formula (I) or (II), or a pharmaceutically acceptable salt thereof or solvate of the foregoing may be administered to an individual in a dosage that corresponds to an acetaminophen equivalent dosage, wherein a compound that contains an acetaminophen moiety (such as a compound of formula (I) or (II), or a pharmaceutically acceptable salt thereof) is an acetaminophen equivalent when assessing an acetaminophen equivalent dosage. However, because compounds detailed herein are believed to provide more efficient and predictable levels of acetaminophen upon ingestion, it is understood that the compounds provided herein may be administered at a dosage that is less than the acetaminophen equivalent dosage in order to achieve comparable in vivo levels of acetaminophen as compared to administration of acetaminophen. In a particular aspect, a compound provided herein, or pharmaceutically acceptable salt thereof, is administered to an individual in a dosage of about 300 mg to about 2.6 g. In other embodiments, the compound is administered in a dosage of about 1.3 g to about 1.9 g. In some of these embodiments, the compound is administered in a liquid formulation where the liquid volume of the dosage is about 1-25 mL. In some of these embodiments, the volume of the dosage is about 10-20 mL. In some embodiments, the liquid volume of the dosage is about 1-10 mL. In some embodiments, the liquid volume of the dosage is about 5-10 mL. In other embodiments, the dosages provided herein are acetaminophen equivalent dosages. In some of these embodiments, the dosage is administered more than once a day. In other embodiments, the dosage is administered once every other day or less. In still other embodiments, the dosage is administered more than once daily, such as twice or thrice daily.

In another aspect, methods of administering low volume/high concentration formulations are provided where the formulations comprise a compound provided herein, such as a compound of formula (I) or (II), or a pharmaceutically acceptable salt thereof or solvate of the foregoing and wherein the compound exhibits enhanced solubility (e.g., water solubility) as compared to the solubility of the acetaminophen. Low volume/high concentration formulations are also provided herein, such as formulations comprising a compound provided herein, such as a compound of formula (I) or (II), or a pharmaceutically acceptable salt thereof or solvate of the foregoing and a pharmaceutically acceptable carrier. A "low volume/high concentration" formulation intends a formulation comprising a carrier and a compound provided herein, such as a compound of formula (I) or (II), or a pharmaceutically acceptable salt thereof or solvate of the foregoing where a given volume of carrier contains a higher molar concentration of compound (or greater acetaminophen equivalents) than is available or obtainable using acetaminophen. Taking the compound of formula (I) as an example, a low volume/high concentration of such compound intends a formulation comprising a carrier and the compound, or a pharmaceutically acceptable salt thereof, wherein the formulation contains a higher molar concentration of compound in a given volume of carrier than is available or obtainable using acetaminophen. Methods of providing low volume/high concentrations of acetaminophen are also provided comprising administering to an individual a low volume/high concentration formulation of a compound as detailed herein (e.g., a compound of formula (I) or (II) or a salt thereof or solvate of the foregoing). In one aspect, the methods entail administering a compound provided herein that results in rapid release of acetaminophen when administered to an individual (e.g., by enzymatic cleavage or hydrolysis). A method of providing a single dose of acetaminophen in an amount that exceeds currently available doses by administering a compound as detailed herein, such as a compound of formula (I) or (II) or a salt thereof or solvate of the foregoing, is also described.

Use of a compound provided herein, such as a compound of formula (I) or (II), or a pharmaceutically acceptable salt thereof or solvate of the foregoing in the manufacture of a medicament for the treatment of a condition that is responsive to acetaminophen is described. In some variations, the condition is pain, fever, inflammation, ischemic injury, or neuronal injury.

In another aspect, the present invention provides a kit comprising a compound provided herein, such as a compound of formula (I) or (II), or a pharmaceutically acceptable salt thereof or solvate of the foregoing, and instructions for use. In some embodiments, the instructions relate to the use of the compound for the treatment or prevention of a disease or condition that is responsive to acetaminophen (e.g., pain, fever, inflammation, ischemic injury (such as myocardial and/or cerebral), or neuronal injury.

In another aspect, the present invention provides a kit comprising a formulation comprising a compound provided herein, such as a compound of formula (I) or (II), or a pharmaceutically acceptable salt thereof or solvate of the foregoing, and instructions for use. In some embodiments, the instructions relate to the use of the compound for the treatment or prevention of a disease or condition that is responsive to acetaminophen (e.g., pain, fever, inflammation, ischemic injury (such as myocardial and/or cerebral), or neuronal injury).

BRIEF DESCRIPTION OF THE DRAWINGS

FIG. 2A illustrates pharmacokinetic parameters for acetaminophen and Test Articles A, B and C following oral administration to rats.

FIG. 2B illustrates pharmacokinetic parameters for acetaminophen and Test Articles A, B and C following intravenous administration to rats.

DETAILED DESCRIPTION OF THE INVENTION

Figure 1A:
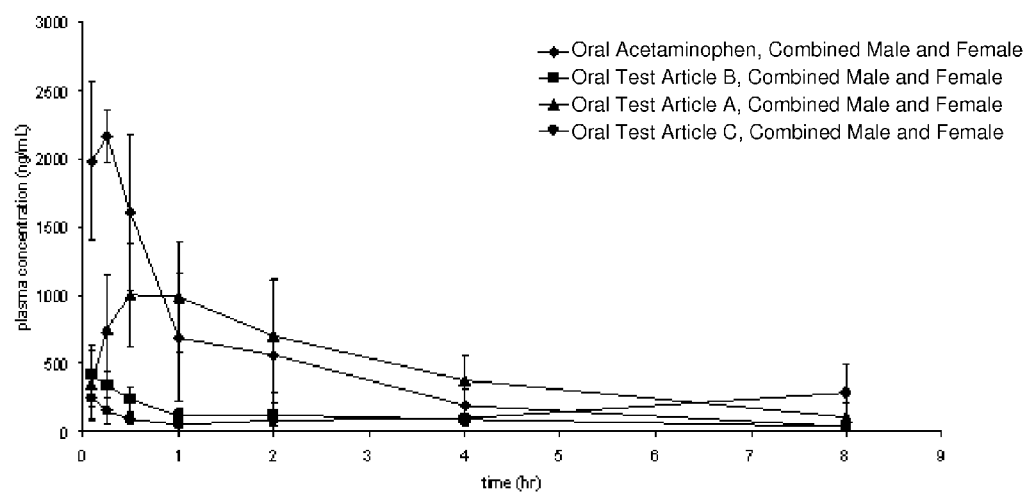
FIG. 1A illustrates the plasma acetaminophen concentration versus time curve for acetaminophen and Test Articles A, B and C following oral administration to rats.

The present invention provides acetaminophen conjugates which have one or more improved properties over existing therapies, including acetaminophen. The acetaminophen conjugates provided herein couple two biologically active compounds, one of which is acetaminophen, such that the two compounds may be released following administration to an individual and/or metabolism of the conjugate. When one of the biologically active compounds is a hepatoprotectant, the compounds provided herein may provide, upon administration to an individual, both acetaminophen and a hepatoprotectant in vivo. It is understood that the conjugate compounds provided herein may exhibit any one or more of the following improved and desired properties over existing therapies, including acetaminophen: (i) increased water solubility; (ii) increased stability (e.g., chemical stability) in an aqueous carrier; (iii) a more desirable safety profile (e.g., reduced toxicity, including reduced hepatotoxicity); (iv) a more predictable exposure to acetaminophen upon administration to an individual, and (v) a more desirable pharmacokinetic profile (e.g., quicker onset of acetaminophen action, and/or more complete conversion to acetaminophen in vivo). In one variation, a compound provided herein exhibits at least two, at least three or all of the foregoing improved and desired properties over existing therapies, including acetaminophen.

A compound as detailed herein, or a salt thereof or solvate of the foregoing, may be particularly suitable for any one or more of: (1) use in formulations comprising the compound or a salt thereof or solvate of the foregoing and an aqueous carrier, such as but not limited to low-volume/high-concentration parenteral formulations for administration, e.g., intravenous injections; (2) administration of acetaminophen in high dosage amount (e.g., amounts that provide more exposure to acetaminophen in vivo than is currently available and/or recommended for administration of acetaminophen alone); (3) use in the prolonged treatment of a condition responsive to acetaminophen (e.g., use of the compound over a longer period of time than is currently recommended for administration of a comparable amount of acetaminophen alone); (4) normalizing exposure to acetaminophen across a population and/or providing predictable levels of acetaminophen to an individual, particularly as compared to administration of acetaminophen; and (5) rapid treatment of a disease or condition that is responsive to acetaminophen, such as pain, fever, inflammation, ischemic injury (such as myocardial and/or cerebral), or neuronal injury.

The inventors have discovered that compound (I) in particular, or a salt thereof or solvate of the foregoing, exhibited striking properties when compared either to acetaminophen or to the known compound (((4-acetamidophenoxy)carbonyl)amino)ethanesulfonic acid, shown below as compound (III).

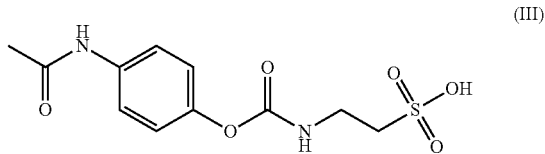 [SMILES: CC(=O)Nc1ccc(OC(=O)NCCS(=O)(=O)O)cc1]

(III)

Compound (III) is described in U.S. Application Publication No. US 20100234452. As detailed herein, compound (I) exhibits favorable properties as compared compound (III).

ABBREVIATIONS AND DEFINITIONS

Nomenclature of some compounds described herein may be identified using ChemDraw Ultra Version 10.0, available from CambridgeSoft®.

As used herein, "more rapid onset of acetaminophen action" refers to the decreased time to onset of acetaminophen action provided by an acetaminophen conjugate as compared to administration of the molar equivalent of acetaminophen (e.g., from currently available formulations such as OFIRMEV® or Perfalgan™) within the same time period through the same route of administration. For example, the rapid release of acetaminophen from compound (I) upon exposure to endogenous enzymatic and/or hydrolytic conditions in vivo may result in more rapid systemic exposure to acetaminophen as compared to administration of the molar equivalent of acetaminophen in the same dosage form to an individual.

As used herein, "treatment", "treating", or "treat" is an approach for obtaining beneficial or desired results, including clinical results. For purposes of this invention, beneficial or desired results include, but are not limited to, one or more of the following: decreasing one or more symptoms of a disease or condition that is responsive to acetaminophen, diminishing the extent of the disease or condition, stabilizing the disease or condition (e.g., preventing the worsening of the disease or condition), delaying or slowing the progression of the disease or condition, ameliorating the disease state or condition, decreasing the dose of one or more other medications required to treat the disease or condition, and increasing the quality of life of an individual who has been or is suspected of having a disease or condition that is responsive to acetaminophen. The disease or condition may be one that is or is believed to be responsive to acetaminophen (e.g., a disease or condition that is accompanied by a fever and/or pain). The disease or condition may be accompanied by inflammation. The disease or condition may be ischemic injury. The disease or condition may be a neuronal injury. In one variation the condition is post-surgical pain and/or fever. In some embodiments, the acetaminophen conjugate and/or formulation comprising the acetaminophen conjugate reduces the severity of one or more symptoms associated with a disease or condition that is responsive to acetaminophen by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the acetaminophen conjugate and/or formulation.

"Responsive to acetaminophen" as used herein refers to a disease or condition, and/or a symptom of a disease or condition which may be treated with acetaminophen.

As used herein, "delaying" means to defer, hinder, slow, retard, stabilize, and/or postpone development of the disease or condition that is responsive to acetaminophen, and/or one or more symptoms of a disease or condition that is responsive to acetaminophen. This delay can be of varying lengths of time, depending on the history of the disease and/or individual being treated. As is evident to one skilled in the art, a sufficient or significant delay can, in effect, encompass prevention, in that the individual does not develop the disease or condition. A method that "delays" development of a disease or condition that is responsive to acetaminophen is a method that reduces the probability of disease or condition development in a given time frame and/or reduces the extent of the disease or condition in a given time frame, when compared to not using the method. Such comparisons are typically based on clinical studies, using a statistically significant number of subjects.

As used herein, an "at risk" individual is an individual who is at risk of developing a disease or condition that is responsive to acetaminophen (e.g., pain, fever, inflammation, ischemic injury (such as myocardial and/or cerebral), or neuronal injuries such as strokes). An individual "at risk" may or may not have a detectable disease or condition, and may or may not have displayed symptoms associated with a detectable disease or condition prior to the treatment methods described herein. "At risk" denotes that an individual has one or more so-called risk factors, which are measurable parameters that correlate with development of a disease or condition. An individual having one or more of these risk factors has a higher probability of developing the disease or condition than an individual without these risk factor(s). Risk factors associated with a disease or condition that is responsive to acetaminophen are known to a skilled artisan. By example only, an individual who is at risk for post-operative pain includes an individual who will undergo (e.g., imminently undergo) or is currently undergoing surgery and is expected to experience post-operative pain as a result thereof.

As used herein, "pharmaceutically acceptable" refers to a material that is not biologically or otherwise undesirable, e.g., the material may be incorporated (such as at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition or who displays one or more of its symptoms. An effective amount may completely or partially prevent the occurrence or recurrence of the disease or condition or symptom thereof and/or may be therapeutic in terms of a partial or complete cure for the disease or condition and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to acetaminophen (e.g., pain, fever, inflammation, ischemic injury (such as myocardial and/or cerebral), or neuronal injury). In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/prevented (e.g., the type of pain), the severity of the condition being treated or prevented, the age, body size, weight, and relative health of the individual, the route and form of administration, and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and an acetaminophen conjugate may be considered to be given in an effective amount if, in conjunction with one or more additional pharmaceutical agents, one or more desirable or beneficial result(s) may be or are achieved.

When used with respect to methods of treatment and/or prevention and the use of the acetaminophen conjugates described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.).

In some variations, the individual has been identified as having one or more diseases or conditions, and/or symptoms thereof described herein. Identification of the diseases or conditions and/or symptoms thereof by a skilled physician is routine in the art (e.g., detection of allergies, cold, cough, flu, pain, etc.) and may also be suspected by the individual or others, for example, due to pain, fever, etc.

In some embodiments, the individual has been identified as susceptible to one or more of the diseases or conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle, or habits.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, adolescents, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

As used herein, "combination therapy" means a first therapy that includes an acetaminophen conjugate in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through same or different routes. In one variation, the combination therapy may include an acetaminophen conjugate and acetaminophen. In some embodiments, the combination therapy optionally includes one or more pharmaceutically acceptable carriers or excipients, non-pharmaceutically active compounds, and/or inert substances.

As used herein, the term "additional pharmaceutical agent," refers to an active agent other than the acetaminophen conjugate (e.g., another drug and/or acetaminophen itself) which is administered to elicit a therapeutic effect. The additional pharmaceutical agent(s) may be directed to (1) a therapeutic effect related to the disease or condition that acetaminophen conjugate compound is intended to treat or prevent (e.g., pain), (2) treat or prevent a symptom of the underlying condition, (3) reduce the appearance or severity of side effects of administering the acetaminophen conjugate, and/or (4) a therapeutic effect related to a disease or condition that is not responsive to acetaminophen or is relatively less responsive to acetaminophen (e.g., insomnia, anxiety, depression, inflammation, nausea, and/or vomiting).

Reference to "about" a value or parameter herein includes (and describes) variations that are directed to that value or parameter per se. For example, a description referring to "about X" includes the description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Unless defined otherwise or clearly indicated by context, all technical and scientific terms and abbreviations used herein have the same meaning as commonly understood by one of ordinary skill in the art to which this invention belongs.

Acetaminophen Conjugates

The invention embraces acetaminophen conjugates, and pharmaceutically acceptable salts thereof and solvates of the foregoing, which may be useful in the treatment of a disease or condition that is responsive to acetaminophen. In some embodiments, the acetaminophen conjugates contain: (i) an acetaminophen moiety and (ii) a moiety of 2-sulfanylethanesulfonic acid or 2-aminoethanesulfinic acid. The moiety of 2-sulfanylethanesulfonic acid or 2-aminoethanesulfinic acid in one aspect is bound to the acetaminophen moiety via a linker positioned at the acetaminophen hydroxyl group. In one aspect, the linker comprises a carbonyl group. In a particular variation, an acetaminophen conjugate is a conjugate of acetaminophen and mesna (mesna is the sodium salt of 2-sulfanylethanesulfonic acid and is an acronym for 2-mercaptoethane sulfonate sodium). In another variation, an acetaminophen conjugate is a conjugate of acetaminophen and 2-aminoethanesulfinic acid (2-aminoethanesulfinic acid is also known as hypotaurine). In one embodiment, the conjugate comprises a moiety of mesna linked to the acetaminophen hydroxyl group via a linker, wherein the linkage comprises a thiocarbonate moiety. In another embodiment, the conjugate comprises a moiety of hypotaurine linked to the acetaminophen hydroxyl group via a linker, wherein the linkage comprises a carbamate moiety.

In one aspect, the acetaminophen conjugate is 2-((4-acetamidophenoxy)carbonylthio)ethanesulfonic acid, as illustrated by formula (I):

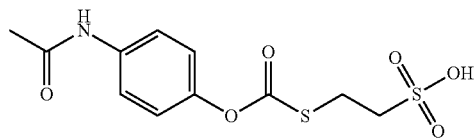

(I)

or a pharmaceutically acceptable salt thereof or solvate of the foregoing.

In one aspect, the pharmaceutically acceptable salt of a compound of formula (I) is an alkali metal salt. In a particular variation, the acetaminophen conjugate is sodium 2-((4-acetamidophenoxy)carbonylthio)ethanesulfonate, as illustrated by formula (Ia):

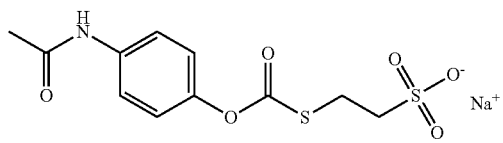

(Ia)

or a solvate thereof.

In another aspect, the acetaminophen conjugate is (((4-acetamidophenoxy)carbonyl)amino)methanesulfinic acid, as illustrated by formula (II):

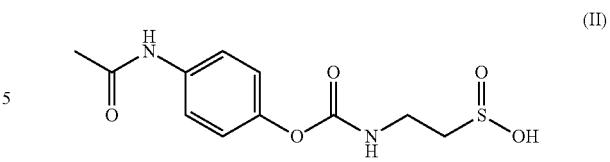

(II)

or a pharmaceutically acceptable salt thereof or solvate of the foregoing.

In one aspect, the pharmaceutically acceptable salt of a compound of formula (II) is an alkali metal salt. In another aspect, the acetaminophen conjugate is sodium (((4-acetamidophenoxy)carbonyl)amino) ethanesulfinate, as illustrated by formula (IIa):

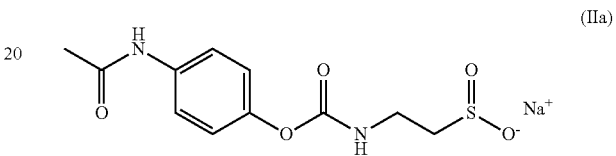

(IIa)

or a solvate of the foregoing.

In some embodiments, the acetaminophen conjugate is in substantially pure form. Unless otherwise stated, "substantially pure" intends a preparation of the acetaminophen conjugate that contains no more than 15% impurity, wherein the impurity denotes compounds other than the acetaminophen conjugate, but does not include other forms of the conjugate (e.g., different salt or non-salt versions of the conjugate). In one variation, a preparation of substantially pure conjugate is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

The invention also embraces all of the solvate, hydrate and/or salt (e.g., pharmaceutically acceptable salt) forms of the acetaminophen conjugates described herein and methods of using the same. In some embodiments, the acetaminophen conjugates of the present invention can exist in unsolvated forms as well as solvated forms (i.e., solvates). The acetaminophen conjugates may also include hydrated forms (i.e., hydrates).

The invention embraces all salts of the compounds described herein, as well as methods of using such salts of the compounds. The invention also embraces all non-salt forms of any salt of a compound described herein, as well as other salts of any salt of a compound named herein. In some embodiments, the salts of the compounds are pharmaceutically acceptable salts. "Pharmaceutically acceptable salts" are those salts which retain at least a portion of the biological activity of the free compounds and which can be administered as drugs or pharmaceuticals to an individual (e.g., a human). In some embodiments, the acetaminophen conjugates are alkali metal or alkaline earth metal salts. In some embodiments, the acetaminophen conjugate is a mono alkaline salt (e.g., mono sodium salt). The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Other salts are also provided and include those known to the skilled artisan, such as those in P. H. Stahl, C. G. Wermuth (Eds), Handbook of Pharmaceutical Salts (Properties, Selection and Use), Wiley-VCH, Weinheim, Germany, 2008 and in Haynes, D. A., et al., J. Pharm. Sci., 2005, 94, 2111-2120.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and dissolution kinetics. Various factors such as the recrystallization solvent, rate of crystallization, and storage temperature may cause a single crystal form to dominate.

In some embodiments, the acetaminophen conjugates exhibit enhanced solubility when compared to acetaminophen. In some embodiments, the acetaminophen conjugates exhibit reduced or no bioactivity or reduced or no affinity for a receptor wherever applicable, when compared to acetaminophen. However, upon administration to an individual, the acetaminophen conjugates release acetaminophen and an additional pharmaceutical agent in vivo (e.g., via hydrolysis or enzymatic cleavage of the conjugate).

The acetaminophen conjugates described herein may be relatively stable under some conditions (e.g., during storage and/or preparation in a saline solution), while being converted to their parent drugs under other conditions (e.g., following introduction into an in vitro or in vivo system, such as administration into an individual). In some embodiments, the conjugate (e.g., a conjugate of formula I or II or a salt or solvate thereof) at, for example, about 0.3 ng/mL or about 15 ng/mL in plasma, or between about 0.3 ng/mL or about 15 ng/mL in plasma) is capable of greater than 10%, or 15%, or 20%, or 25%, or 30%, or 35%, or 40%, or 45%, or 50%, or 60%, or 75% conversion to acetaminophen after about any of 1 min, 5 min, 10 min, 15 min, 20 min, or 30 min, or 45 min, or 1 hr at 37° C. In some embodiments, the conjugate (e.g., a conjugate of formula I or II or a salt or solvate thereof) at, for example, about 0.3 µg/mL or about 15 µg/mL in human plasma, or between about 0.3 µg/mL or about 15 µg/mL in human plasma) is capable of greater than about 30%, or about 45% conversion to acetaminophen after about 1 hr at 37° C. In some of these embodiments, the acetaminophen conjugates are not capable of said conversion to acetaminophen in water, propylene glycol and/or saline at room temperature. For example, in some of these embodiments, the conjugate is not capable of more than any of about 5%, or 10%, or 20%, or 25%, or 30% or 40%, or 60%, or 70% conversion to parent drug at 30 min or 60 min in water or propylene glycol at room temperature. In one embodiment, the acetaminophen conjugate (e.g., a conjugate of formula I or II or a salt or solvate thereof) at a concentration of about 15 µg/mL in human plasma (or 0.3 µg/mL, or between 0.3 µg/mL and 15 µg/mL) at 37° C. is capable of greater than 30% conversion to the parent drug at 45 min, and is not capable at the same concentration in water at room temperature of more than 30% conversion at 45 min. In some embodiments, the conjugate (e.g., a conjugate of formula I or II or a salt or solvate thereof) is capable of at least about any one of 10%, 20%, 30%, 40%, 50%, 60%, 70%, 80%, or 90% increased conversion to parent drug in human plasma at 37° C. compared to water at room temperature after the same time of exposure.

Formulations

The acetaminophen conjugates described herein can be in formulations (including pharmaceutical compositions) with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either alone or together with one or more additional pharmaceutical agents, provided that the additional components are pharmaceutically acceptable for the particular disease or condition to be treated. In some embodiments, the formulation may include combinations of two or more of the additional components as described herein (e.g., 2, 3, 4, 5, 6, 7, 8, or more additional components). In one variation, the formulations may comprise two or more acetaminophen conjugates. In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21$^{st}$ edition (2005).

The formulations may vary or be tailored according to the condition to be treated, the amount of compound to be administered, the condition of the individual, and other variables that will readily be apparent to one of ordinary skill in the art in view of the teachings provided herein.

In some embodiments, the formulation comprising an acetaminophen conjugate (e.g., formulations amenable to parenteral administration) is an aqueous formulation with a pH from about 3.5 to about 9.5, or from about 4.5 to about 8.5, or from about 5.0 to about 9.0, or from about 5.5 to about 8.5, or from about 6.0 to about 8.0, or from about 6.5 to about 8.0, or from about 7.0 to about 8.0, or about 7.4.

Formulations comprising a conjugate of the formula (I) or (II), or a salt thereof or solvate of the foregoing, and saline are provided. In one aspect, such formulations are at physiological pH (about 7.4). Such formulations may be amenable to storage and subsequent use with the conjugate remaining intact for a period of time (e.g., during storage) and converted to acetaminophen after administration to an individual (e.g., an adult, adolescent, child, or infant). In some embodiments, the conjugate is stored as a dry powder and the formulation is generated by dissolving the dry powder in saline prior to administration. In one aspect, conjugate formulations are provided, e.g., formulations comprising the molar equivalent of about any of 50 mg/mL, 75 mg/mL, 100 mg/mL, 125 mg/mL, 150 mg/mL, 175 mg/mL, or 200 mg/mL of acetaminophen, wherein molar equivalent is the amount of conjugate that would result in the indicated amount of acetaminophen upon complete conversion. For any amount (e.g., dosage) of conjugate described herein, also contemplated is the molar conjugate equivalent for that amount of acetaminophen. Single bolus formulations are also provided, e.g., up to about any of 5 mL, 10 mL, or 15 mL (at, for example, the molar conjugate equivalent of about 1450 mg to about 1600 mg of acetaminophen).

Kits

The invention also provides kits containing materials useful for the treatment or prevention of a condition that is responsive to acetaminophen (e.g., pain). The kits may contain an acetaminophen conjugate of the invention and instructions for use. The kits may comprise a container with a label. Suitable containers include, for example, bottles, vials, and test tubes. The containers may be formed from a variety of materials such as glass or plastic. The containers may hold an acetaminophen conjugate or a formulation of an acetaminophen conjugate (e.g., a formulation further comprising one or more additional pharmaceutical agents). The label on the container may indicate that the acetaminophen conjugate or the formulation is used for treating or suppressing a condition that is responsive to acetaminophen (e.g., pain), and may also indicate directions for either in vivo or in vitro use, such as those described herein.

The invention also provides kits comprising one or more of the acetaminophen conjugate of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions responsive to acetaminophen (e.g., pain and/or fever), or to suppress one or more such conditions.

In certain embodiments the kits may include a dosage amount of at least one formulation as disclosed herein. In one aspect, dosage forms correspond to dose that exceed the molar equivalent of 4 g/day of acetaminophen. Kits may also comprise a means for the delivery of the formulation thereof.

The kits may include additional pharmaceutical agents for use in conjunction with the formulation described herein. In some variations, the additional pharmaceutical agent(s) may be one or more analgesic drug(s). These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and/or administration of a formulation comprising an acetaminophen conjugate of the invention. Information detailing possible side effects of the formulation, and any other relevant information may also be enclosed. The instructions may be in any suitable format, including, but not limited to, printed matter, videotape, computer readable disk, optical disc or directions to internet-based instructions.

In another aspect of the invention, kits for treating an individual who suffers from or is susceptible to a disease or condition described herein (e.g., pain and/or fever) are provided, comprising a first container comprising a dosage amount of a conjugate composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

The kits may include the composition as described herein packaged in either a unit dosage form or in a multi-use form. The kits may also include multiple units of the unit dose form.

Unit dosage forms of an acetaminophen conjugate, or a pharmaceutically acceptable salt thereof or solvate of the foregoing, are also provided.

Methods of Treatment

The acetaminophen conjugate of the present invention may be used to treat a disease or condition that is responsive to acetaminophen (e.g., pain and/or fever). In one embodiment, the invention provides a method of treating a disease or condition that is responsive to acetaminophen comprising administering to an individual an effective amount of an acetaminophen conjugate (e.g., a compound of formula (I) or (II), or a pharmaceutically acceptable salt thereof or solvate of the foregoing). In some embodiments, the individual is at risk of developing a disease or condition that is responsive to acetaminophen. In some embodiments, methods of treating pain, fever, inflammation, ischemic injury (such as myocardial and/or cerebral), or neuronal injury in an individual, comprising administering to the individual an effective amount of an acetaminophen conjugate, or pharmaceutically acceptable salt thereof or solvate of the foregoing, are provided. In one variation, the individual is post-operative and has or is believed to have or developed post-operative pain. In one variation, the conjugate is administered prophylactically for post-operative pain. In one variation, the individual is not amenable to oral administration of acetaminophen. In yet another variation, the individual is not amenable to the existing other acetaminophen formulations.

The invention embraces methods of treating pain of any etiology, including acute and chronic pain, and any pain in which acetaminophen analgesic is prescribed. Examples of pain include post-surgical pain, post-operative pain (including dental pain), migraine, headache and trigeminal neuralgia, pain associated with burn, wound or kidney stone, pain associated with trauma (including traumatic head injury), neuropathic pain (e.g., peripheral neuropathy and postherpetic neuralgia), pain associated with musculo-skeletal disorders, strains, sprains, contusions, fractures, myalgia, rheumatoid arthritis, osteoarthritis, cystitis, pancreatitis, inflammatory bowel disease, ankylosing spondylitis, seronegative (non-rheumatoid) arthropathies, non-articular rheumatism and peri-articular disorders, and pain associated with cancer (including "break-through pain" and pain associated with terminal cancer). Examples of pain with an inflammatory component (in addition to some of those described above) include rheumatic pain, pain associated with mucositis, and dysmenorrhea (e.g., primary dysmenorrhea). In some variations, the methods and formulations of the present invention are used for treatment or prevention of post-surgical pain and/or cancer pain. In some variations, the methods and compositions of the present invention are used for treatment or prevention of pain that is selected from the group consisting of pain associated with infectious disease, pain associated with surgery, trauma, osteoarthritis, rheumatoid arthritis, lower back pain, fibromyalgia, postherpetic neuralgia, diabetic neuropathy, HIV-associated neuropathy and complex regional pain syndrome. In some variations, the methods and compositions of the present invention are used for treatment or prevention of pain associated with infectious disease, including influenza, tropical diseases and the like, which are often accompanied with high fevers.

In some variations, the methods and compositions of the present invention (e.g., a compound of the formula (I) or (II) or a pharmaceutically acceptable salt thereof or solvate of the foregoing) are used for treatment or prevention of pain and/or fever (e.g., in adults, adolescents, children and/or infants). In some embodiments, the methods and compositions of the present invention (e.g., a compound of the formula (I) or (II) or a pharmaceutically acceptable salt thereof or solvate of the foregoing) are used for treatment of pain, such as acute pain (e.g., acute pain following surgery, such as orthopedic surgery of adults, children, and/or infants). In some embodiments, the methods and compositions of the present invention (e.g., a compound of the formula (I) or (II) or a pharmaceutically acceptable salt thereof or solvate of the foregoing) are used for treatment or prevention of fever, such as endotoxin-induced fever (e.g., endotoxin-induced fever in adults, adolescents, children, and/or infants). In some embodiments, the methods and compositions of the present invention (e.g., a compound of the formula (I) or (II) or a pharmaceutically acceptable salt thereof or solvate of the foregoing) are used for treatment or prevention of fever in children and/or infants. In some embodiments, the fever is selected from low-grade fever, moderate fever, high-grade fever and hyperpyrexia fever. In some embodiments, the fever is selected from Pel-Ebstein fever, continuous fever, intermittent fever, and remittent fever.

In some variations of the methods, the hepatotoxicity, potential hepatotoxicity, and/or amount of hepatotoxins in an individual following administration of the acetaminophen conjugate (e.g., a compound of the formula (I) or (II) or a pharmaceutically acceptable salt thereof or solvate of the foregoing) is reduced relative to administration of acetaminophen under the same conditions. In some variations, the toxic effects or potential toxic effects on the liver of the individual following administration of the acetaminophen conjugate (e.g., a compound of the formula (I) or (II) or a pharmaceutically acceptable salt thereof or solvate of the foregoing) is reduced relative to administration of acetaminophen under the same conditions.

The invention embraces methods of reducing the level of hepatotoxicity of acetaminophen in an individual, comprising administering to the individual an acetaminophen conjugate (e.g., a compound of the formula (I) or (II) or a pharmaceutically acceptable salt thereof or solvate of the foregoing), wherein the level of hepatotoxicity is reduced compared to administration of acetaminophen of equimolar or comparable dose. The invention also embraces methods of reducing the level of liver toxicity of acetaminophen in an individual, comprising administering to the individual an acetaminophen conjugate (e.g., a compound of the formula (I) or (II) or a pharmaceutically acceptable salt thereof or solvate of the foregoing). In some of these methods, hepatotoxicity is reduced while concurrently treating the individual for a disease or condition that is responsive to acetaminophen (e.g., pain and/or fever).

In some embodiments, the invention embraces a method of providing a more rapid onset of acetaminophen action in an individual in need of acetaminophen therapy, the method comprising administering to the individual an effective amount of a compound of formula (I) or (II), or a pharmaceutically acceptable salt thereof or solvate of the foregoing, wherein the compound, upon administration to an individual, provides a more rapid onset of acetaminophen action as compared to administration of acetaminophen. In one variation, administration of the acetaminophen conjugate or salt thereof advances the onset of acetaminophen action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of acetaminophen. In some embodiments, the conjugates exhibit little or no delay in the onset of acetaminophen action (e.g., upon I.V. administration of a conjugate).

In some embodiments, the invention embraces a method of providing acetaminophen to an individual, the method comprising administering an acetaminophen conjugate (e.g., a compound of the formula (I) or (II) or a pharmaceutically acceptable salt thereof or solvate of the foregoing), wherein the acetaminophen conjugate converts to acetaminophen. Also provided are methods of providing acetaminophen to an individual by administering an acetaminophen conjugate (e.g., a compound of the formula (I) or (II) or a pharmaceutically acceptable salt thereof or solvate of the foregoing), where the conjugate converts to acetaminophen in vivo. In one aspect, the conjugate (e.g., a compound of the formula (I) or (II) or a pharmaceutically acceptable salt thereof or solvate of the foregoing) results in conversion to acetaminophen within about 1, 5, 10, 15, or 30 min following administration. Conversion may be measured by techniques known in the art, including those detailed in the Experimental section herein. In some embodiments, the invention embraces methods of providing acetaminophen to an individual (e.g., an individual in need of acetaminophen therapy), the method comprising administering to the individual an effective amount of an acetaminophen conjugate (e.g., a compound of the formula (I) or (II) or a pharmaceutically acceptable salt thereof or solvate of the foregoing) wherein greater than about any of 10%, or 15%, or 20%, or 25%, or 30%, or 35%, or 40%, or 45%, or 50%, or 60%, or 75% or 85%, or 90%, or 95% of the conjugate is converted to acetaminophen after less than about any of 1 min, 3 min, 5 min, 10 min, 20 min, or 30 min, or 45 min, or 1 hr following administration. In some embodiments, the method comprises administering to the individual an effective amount of an acetaminophen conjugate (e.g., a compound of the formula (I) or (II) or a pharmaceutically acceptable salt thereof or solvate of the foregoing) wherein greater than about 10% or about 20% of the conjugate is converted to acetaminophen after less than about 1 min or about 3 min following administration.

In some embodiments, the invention embraces a method of providing acetaminophen to an individual (e.g., an individual in need of acetaminophen therapy), the method comprising administering to the individual (e.g., intravenously) an effective amount of an acetaminophen conjugate (e.g., a compound of the formula (I) or (II) or a pharmaceutically acceptable salt thereof or solvate of the foregoing) wherein the resulting concentration of acetaminophen (e.g., at about any of 10 min, or 20 min, or 30 min, or 45 min, or 1 hr, or 2 hr, or 3 hr following administration) is about any of 50%, or 40%, or 30%, or 25%, or 20%, or 15%, or 10%, or 5% more than the concentration of acetaminophen obtained upon administration of an equimolar dose of acetaminophen administered under the same conditions. For example, in some embodiments, a method of providing acetaminophen to an individual in need of acetaminophen therapy is provided, the method comprising intravenously administering to the individual an effective amount of an acetaminophen conjugate (e.g., a compound of the formula (I) or (II) or a pharmaceutically acceptable salt thereof or solvate of the foregoing) wherein the resulting concentration of acetaminophen or a metabolite thereof (e.g., at about 30 min or 1 hr following administration) is about 15% or about 5% more than the concentration of acetaminophen obtained upon administration of an equimolar dose of acetaminophen administered under the same conditions.

The acetaminophen conjugates detailed herein may also confer hepatoprotection from acetaminophen by virtue of the in vivo generation of 2-sulfanylethanesulfonic acid or 2-aminoethanesulfinic acid. Mesna has been demonstrated to have a protective effect against acetaminophen-induced hepatorenal oxidative damage in mice (G. Sener, et al., J. Appl. Toxicol. 2005: 20-29). Hypotaurine has been demonstrated to attenuate the liver injury and the biochemical changes induced by APAP when administered as a pre-treatment to rats. (M. Archarya et al., J. Biomedical Sci., 2010 17(Suppl 1):S35). Thus, also provided are methods of reducing the hepatotoxicity of acetaminophen comprising administering to an individual an effective amount of an acetaminophen conjugate provided herein (e.g., a compound of the formula (I) or (II) or a pharmaceutically acceptable salt thereof or solvate of the foregoing) wherein administration of the conjugate results in reduced hepatotoxicity to the individual as compared to administration of an equimolar dose of acetaminophen.

In some embodiments, the invention embraces a method of providing acetaminophen and a hepatoprotectant to an individual, the method comprising administering an acetaminophen conjugate (e.g., a compound of the formula (I) or (II) or a pharmaceutically acceptable salt thereof or solvate of the foregoing), wherein the conjugate converts to acetaminophen and a hepatoprotectant. In one aspect, the conjugate is of the formula (I), or a pharmaceutically acceptable salt thereof or solvate of the foregoing, and the hepatoprotectant is 2-sulfanylethanesulfonic acid. In another aspect, the conjugate is of the formula (II), or a pharmaceutically acceptable salt thereof or solvate of the foregoing, and the hepatoprotectant is 2-aminoethanesulfinic acid. Also provided are methods of providing acetaminophen and a hepatoprotectant to an individual by administering an acetaminophen conjugate (e.g., a compound of the formula (I) or (II) or a pharmaceutically acceptable salt thereof or solvate of the foregoing), where the conjugate converts to acetaminophen and a hepatoprotectant in vivo. In one aspect, the conjugate (e.g., a compound of the formula (I) or (II) or a pharmaceutically acceptable salt thereof or solvate of the foregoing) results in conversion to acetaminophen within about 1, 5, 10, 15, or 30 min following administration. Conversion may be measured by techniques known in the art, including those detailed in the Experimental section herein. In some embodiments, the invention embraces methods of providing acetaminophen and a hepatoprotectant to an individual (e.g., an individual in need of acetaminophen and/or hepatoprotectant therapy), the method comprising administering to the individual an effective amount of an acetaminophen conjugate (e.g., a compound of the formula (I) or (II) or a pharmaceutically acceptable salt thereof or solvate of the foregoing) wherein greater than about any of 10%, or 15%, or 20%, or 25%, or 30%, or 35%, or 40%, or 45%, or 50%, or 60%, or 75% or 85%, or 90%, or 95% of the conjugate is converted to acetaminophen and the hepatoprotectant after less than about any of 1 min, 3 min, 5 min, 10 min, 20 min, or 30 min, or 45 min, or 1 hr following administration. In some embodiments, the method comprises administering to the individual an effective amount of an acetaminophen conjugate (e.g., a compound of the formula (I) or (II) or a pharmaceutically acceptable salt thereof or solvate of the foregoing) wherein greater than about 10% or about 20% of the conjugate is converted to acetaminophen and the hepatoprotectant after less than about 1 min or about 3 min following administration.

In some embodiments, the invention embraces a method of providing acetaminophen and a hepatoprotectant to an individual (e.g., an individual in need of acetaminophen and/or hepatoprotectant therapy), the method comprising administering to the individual (e.g., intravenously) an effective amount of an acetaminophen conjugate (e.g., a compound of the formula (I) or (II) or a pharmaceutically acceptable salt thereof or solvate of the foregoing) wherein the resulting concentration of acetaminophen (e.g., at about any of 10 min, or 20 min, or 30 min, or 45 min, or 1 hr, or 2 hr, or 3 hr following administration) is about any of 50%, or 40%, or 30%, or 25%, or 20%, or 15%, or 10%, or 5% more than the concentration of acetaminophen obtained upon administration of an equimolar dose of acetaminophen administered under the same conditions. For example, in some embodiments, methods of providing acetaminophen and a hepatoprotectant to an individual in need of acetaminophen and/or hepatoprotectant therapy are provided, the methods comprising intravenously administering to the individual an effective amount of an acetaminophen conjugate (e.g., a compound of the formula (I) or (II) or a pharmaceutically acceptable salt thereof or solvate of the foregoing) wherein the resulting concentration of acetaminophen or metabolite thereof (e.g., at about 30 min or 1 hr following administration) is about 15% or about 5% more than the concentration of acetaminophen obtained upon administration of an equimolar dose of acetaminophen administered under the same conditions.

Methods of administering a higher dose of acetaminophen to an individual than may be safely provided by administration of an equimolar dose of acetaminophen are also provided. It is believed that the conjugates may provide a protecting effect against acetaminophen hepatotoxicity, thus enabling higher doses of the conjugates to be safely administered to an individual when compared to doses of acetaminophen that may be safely administered to an individual. In one aspect, acetaminophen is provided to the individual by administering an acetaminophen conjugate (e.g., a compound of the formula (I) or (II) or a pharmaceutically acceptable salt thereof or solvate of the foregoing) in a dose and over a time period unsafe for administration of acetaminophen (and/or formulations of acetaminophen) under the same conditions. For example, methods of providing greater than a 4 g/day dose of acetaminophen to an individual are provided by administering to the individual an acetaminophen conjugate (e.g., a compound of the formula (I) or (II) or a pharmaceutically acceptable salt thereof or solvate of the foregoing) in a daily dosage that, upon administration to an individual, provides greater than 4 g/day of acetaminophen in vivo. In one aspect, the methods employ liquid formulations (e.g., saline) of a conjugate detailed herein. Methods may also employ different formulations (e.g., I.V. administration followed by oral doses).

Combination Therapy

The acetaminophen conjugates described herein may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, or in conjunction with (e.g., prior to, concurrently with, or after) additional treatment modalities. The acetaminophen conjugates as described herein may be administered before, concurrently with, or after the administration of one or more of the additional pharmaceutical agents. The acetaminophen conjugates described herein may also be administered in conjunction with (e.g., prior to, concurrently with, or after) agents to alleviate the symptoms associated with either the condition or the treatment regimen.

In some embodiments of the formulations and methods of the present invention, the acetaminophen conjugates are used in combination with one or more additional pharmaceutical agents. Representative additional pharmaceutical agents include opioids (natural, semi-synthetic, or synthetic), non-steroidal anti-inflammatory drugs (NSAIDs), benzodiazepines, barbiturates and other compounds, such as caffeine. Examples of compounds contemplated for combination with conjugates of the current invention include, but are not limited to, codeine, morphine, hydrocodone, hydromorphone, levorphanol, aspirin, ketorolac, ibuprofen, naproxen, caffeine, tramadol, dextropropoxyphene, methylhexital, diazepam, lorazepam, midazolam, propoxyphene, ketoprofen, flurbiprofen, etodolac, diclofenac, misoprostol, meloxicam, piroxicam, doxylamine, pamabrom, carisoprodol, gabapentin, pregabalin, duloxetin and butalbital.

One potential advantage of a combination formulation is that the formulation may induce analgesia beyond the ceiling effect of acetaminophen administered without a concomitant hepatoprotectant without approaching the toxic or nearly toxic dose levels of acetaminophen. Combinations of the acetaminophen conjugates with benzodiazepines such as diazepam, lorazepam, midazolam or any other benzodiazepines, may be used for treatment of pre- and postoperative anxiety in addition to the treatment of e.g., analgesia. Such combination may be particularly useful in dental surgeries (e.g., third molar extraction).

The above additional pharmaceutical agents to be employed in combination with the acetaminophen conjugates of the invention may be used in therapeutic amounts, such as those indicated in the PHYSICIANS' DESK REFERENCE (PDR) 53rd Edition (1999), or such therapeutically useful amounts as would be known to one of ordinary skill in the art.

Additional pharmaceutical agents (e.g., analgesic drugs) administered with one or more of the acetaminophen conjugates of the invention can be administered at the recommended maximum clinical dosage or at lower doses. Dosage levels of the additional pharmaceutical agents in the formulations of the invention may be varied so as to obtain a desired therapeutic response depending on the route of administration, severity of the disease and the characteristics and response of the patient. The combination can be administered as separate formulations or as a single dosage form containing both agents. When administered as a combination, the acetaminophen conjugates can be formulated as separate formulations, which are given at the same time or different times, or the acetaminophen conjugates, can be given as a single formulation.

As will be well appreciated by the skilled artisan, for particular conditions, different additional pharmaceutical agent(s) and/or additional treatment modality(ies) may be employed.

In some embodiments, an acetaminophen conjugate of the current invention may be formulated and/or administered with acetaminophen itself. Such combination therapy may provide an initial therapeutic amount of the parent drug, followed by a delayed and/or prolonged parent drug activity from the conjugate. For example, a combination of a compound of the formula (I) or (II), or a pharmaceutically acceptable salt thereof or solvate of the foregoing, with acetaminophen may be employed. Such formulations may permit a decreased dosing frequency. Alternatively, an initial dose of a compound of the formula (I) or (II) or a pharmaceutically acceptable salt thereof or solvate of the foregoing (e.g., as a low volume/high concentration dose to treat post-operative pain and/or fever) may be followed by administration of acetaminophen to treat pain and/or fever (e.g., after discharge from a hospital or surgical setting).

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, surgery or radiotherapy. As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the acetaminophen conjugates (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

Dosing and Methods of Administration

The acetaminophen conjugates and formulations described herein will generally be used in an amount effective to achieve the intended result, for example in an effective amount to treat or prevent the particular condition being treated or prevented (e.g., pain and/or fever). The amount of the acetaminophen conjugate or formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein. Dosages may also be estimated using in vivo animal models.

The amount of acetaminophen conjugate that may be combined with the carrier materials to produce a single dosage form may vary depending upon the host to which the acetaminophen conjugate is administered and the particular mode of administration, in addition to one or more of the variety of factors described above. A pharmaceutical unit dosage chosen may be fabricated and administered to provide a defined final concentration of drug in the blood, tissues, organs, or other targeted region of the body. The effective amount for a given situation can be readily determined by routine experimentation and is within the skill and judgment of the ordinary clinician.

In some embodiments, the dosage of acetaminophen conjugate required to obtain the same blood level concentration as acetaminophen is lower due to the increased solubility and/or metabolic profile (e.g., less drug loss due to first pass metabolism in the liver) of the conjugate. In some embodiments, the required dosage of the conjugate to obtain the same blood level concentration as the acetaminophen is 1.2, 2, 5, 7.5, 10, 15, 20, 50, or 100 times lower than acetaminophen.

Examples of acetaminophen conjugate dosages (alone or in combination) which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered, alone or in combination, in a single daily dose, or the total daily dosage may be administered in divided dosage of two, three, four, five, or six times daily. The compounds may be administered less than once daily, e.g., one weekly, twice weekly or thrice weekly.

The frequency and duration of administration of the acetaminophen conjugate will depend on the condition being treated, the condition of the individual, and the like. The formulation may be administered to the individual one or more times, for example, 2, 3, 4, 5, 10, 15, 20, or more times. The formulation may be administered to the individual, for example, more than, equal to, or less than once a day, 2 times a day, 3 times a day, or more than 3 times a day; or 1-6 times a day, 2-6 times a day, or 4-6 times a day. The formulation may also be administered to the individual, for example, less than once a day, for example, every other day, every third day, every week, or less frequently. The formulation may be administered over a period of days, weeks, or months.

The acetaminophen conjugates of the invention may be administered enterally (e.g., orally or rectally), parenterally (e.g., by injection (such as intravenously or intramuscularly), or by inhalation (e.g., as mists or sprays), or topically, in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g., via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The acetaminophen conjugates may be mixed with pharmaceutically acceptable carriers, adjuvants, and vehicles appropriate for the desired route of administration. The route of administration may vary according to the condition to be treated. Additional methods of administration are known in the art.

In some embodiments of the methods, the route of administration is oral. In some embodiments, formulations are suitable for oral administration. The acetaminophen conjugates described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

In some embodiments, the acetaminophen conjugate is administered parenterally (e.g., intravenously or intramuscularly). Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

In some embodiments are provided high doses of acetaminophen conjugate in a low volume (e.g., in a low volume of saline). Non-limiting examples of an effective amount (e.g., for parenteral administration, such as intravenous or intramuscular), include the acetaminophen conjugate at a dosage range of from about 20 mg per day to about 8 g per day, or from about 60 mg per day to about 6 g, or from about 200 mg per day to about 4 g, or from about 300 mg to about 2.6 g per day, or from about 500 mg to about 2 g per day. In some embodiments, the effective amount for parenteral (e.g., intravenous or intramuscular) administration is a dose volume of about 200 mg to about 5 g, or about 500 mg to about 4 g, or about 750 mg to about 3 g, or about 1 g to about 2.5 g, or about 1.3 g to about 1.9 g, in about 1 mL to about 30 mL, or about 1 mL to about 25 mL, or about 5 mL to about 20 mL, or about 5 mL to about 15 mL or about 10 mL to about 15 mL, or about 5 mL to about 10 mL. In some of these embodiments, the acetaminophen conjugate is administered in a solution at a concentration of about 10 mg/mL to about 1000 mg/mL, or about 25 mg/mL to about 750 mg/mL, or about 50 mg/mL to about 500 mg/mL, or about 75 mg/mL to about 400 mg/mL, or about 100 mg/mL to about 300 mg/mL, or about 150 mg/mL to about 250 mg/mL.

The invention also includes formulations of acetaminophen conjugates administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The acetaminophen conjugates of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and/or metabolizable lipid capable of forming liposomes may be used. The present formulations in liposome form can contain, in addition to an acetaminophen conjugate, stabilizers, preservatives, excipients, and the like. In some embodiments, the lipids are the phospholipids and/or phosphatidyl cholines (lecithins), natural and/or synthetic. Methods to form liposomes are known in the art. See, for example, Prescott, Ed., *Methods in Cell Biology*, Volume XIV, Academic Press, New York, N.W., p. 33 et seq (1976).

Synthetic Methods

The compounds of the invention may be prepared using a number of methods familiar to one of skill in the art. The discussion below is offered to illustrate methods available for use in assembling the compounds of the invention and is not intended to limit the scope of the reactions or reaction sequences and/or conditions that are useful in preparing compounds of the invention.

The invention also embraces methods of preparing the conjugates described herein. In one aspect is provided a process for preparing a compound of formula (I) or (II) or a salt thereof.

EXAMPLES

The present invention will be understood more readily by reference to the following examples, which are provided by way of illustration and are not intended to be limiting of the present invention.

General Synthetic Experimental Protocols

All reagents and solvents were purchased from commercial suppliers and used without further purification.

Proton NMR spectra (300 MHz) were recorded on a Varian AS 300 NMR spectrometer and data processing computation. DMSO-$d^6$ (99.9% D), CDCl$_3$ (99.8% D), or deuterium oxide D$_2$O (99.8% D) were used as solvents unless otherwise noted. The residual DMSO-$d^5$, CHCl$_3$, or HDO solvent signals were used for calibration of individual spectra. Analytical thin layer chromatography (TLC) was performed using Whatman, Schleicher & Schuell TLC MK6F silica gel plates (2.5×7.5 cm, 250 μm layer thickness). Dyeing or staining reagents for TLC detection and visualization were prepared according methods known in the art. Analytical LC/MS was performed on a Thermo Finnigan separation module equipped with a Thermo Finnigan LCQ Advantage unit and a Waters symmetry C-18 4.6×75 mm column. Preparative HPLC purification of final products was performed with Dynamax Model SD 200 HPLC equipped with a Phemomenex Axia Gemini 10u C18 100A Column 100×21.20 mm. Analytical HPLCs were performed on a Waters 2695 HPLC system equipped with an Agilent Eclipse XDB-C8 4.5×100 mm column and a Waters 2996 Photodiode Array Detector. Gradients of acetonitrile/water mixtures containing 0.1 vol-% of formic acid were used in both analytical and preparative HPLC procedures. Compound isolation from aqueous solvent mixtures, e.g., acetonitrile/water containing 0.1 vol-% of formic acid, was accomplished by primary lyophilization (freeze drying) of the frozen solutions under reduced pressure at room temperature using manifold freeze dryers such as Labconco Freeze Dry System/Freezone 2.5 equipped with a standard high vacuum pump. Optionally, and if the isolated compound had ionizable functional groups such as a carboxylic acid, sulfinic acid, and/or sulfonic acid the lyophilization process was conducted in the presence of one molar equivalent (per acid functionality) of a suitable alkali metal or alkali earth metal source, e.g., a carbonate, a bicarbonate, an oxide, an acetate, or a hydroxide, to yield the purified compound(s) as the corresponding alkali metal or alkali earth metal salt of the carboxylic, sulfinic, or sulfonic acid.

General Procedure for the Preparation of Alkali Metal Salts

Procedure A:

Depending on its individual solubility, 1.0 equivalents of an amino acid derivative, i.e., a natural or unnatural amino acid, a sulfinic acid, or a sulfonic acid, etc., are dissolved in distilled or deionized (DI) water. In the case of amino acids susceptible to oxidation and to prevent oxidative side reactions, the water can optionally be degassed prior to use using methods know in the art including repeated freeze/thawing cycles, nitrogen purging with or without heating/vacuum, or sonication in an ultrasound bath. Under a nitrogen atmosphere/blanket, an equimolar amount (with respect to the ionizable functional groups in the acid derivative) of any suitable alkali metal source, e.g., a 1.0 N aqueous sodium hydroxide (NaOH$_{(aq.)}$) or potassium hydroxide (KOH$_{(aq.)}$) solution, is added dropwise to the reaction mixture using a syringe. Alternatively, an equimolar amount of any other suitable alkali metal source, e.g., solid NaOH or KOH, is added directly and in small portions to the (amino) acid solution. The reaction mixture is optionally gently heated from about 30° C. to about 60° C. and/or sonicated to ensure complete salt formation and dissolution. The solvent is removed to dryness under reduced pressure using a rotary evaporator. Alternatively, the solvents are frozen (e.g., dry ice/acetone bath) followed by lyophilization under reduced pressure to yield the corresponding alkali metal salt of the (amino) acid derivatives typically as colorless solids (powders). The residue is subsequently dissolved in a sufficient volume of (optionally degassed) water in a round bottom flask or vial and the solution is used directly in the next step without further purification or isolation procedures.

Procedure B:

One (1.0) equivalents of the 2-aryloxycarbonyl-functionalized derivative of the corresponding acid are dissolved in (optionally degassed) water (approximately 1-3 mL/1.0 mmol). To this solution are added 1.0 equivalents of sodium hydrogencarbonate (NaHCO$_3$) or any other suitable alkali metal source dissolved in (optionally degassed) water (approximately 1-3 mL/1.0 mmol). The reaction mixture is optionally sonicated and/or agitated/vortexed for about three (3) to about ten (10) minutes to ensure complete dissolution and formation of a homogeneous solution of the components. If necessary, the reaction mixture is further degassed by applying light vacuum followed by purging with nitrogen. The solvent is removed under reduced pressure using a rotary evaporator with gentle heating (about 30° C. to about 40° C. water bath temperature). Alternatively, the solvents are frozen (e.g., dry ice/acetone bath) followed by lyophilization under reduced pressure to yield the corresponding sodium or alkali metal salt of the 2-aryloxycarbonyl-functionalized derivative of the corresponding acid typically as colorless solids (powders).

General Method for the Reaction of Alkali Metal Salts of Amino Acid Derivatives with 4-Acetamidophenyl 4-Nitrophenyl Carbonate (3)

A solution of 1.0-1.05 equivalents of the appropriate (amino) acid alkali metal salt in (optionally degassed) water (approximately 1-2 mL/3.0 mmol) is subsequently added (optionally under a nitrogen atmosphere) to a solution of 1.0 equivalents of 4-acetamidophenyl 4-nitrophenyl carbonate 3 in acetonitrile (MeCN) (approximately 10 mL/3.0 mmol). Optionally, the reaction mixture is further degassed by applying light vacuum followed by purging with nitrogen. The reaction mixture is stirred at room temperature for overnight. The reaction course is followed by LC/MS. After consumption of the starting materials and completion of the reaction, the pH of the reaction mixture is adjusted to about four (4) using 1.0 N hydrochloric acid (HCl$_{(aq.)}$). The solution is subsequently washed with dichloromethane (DCM) (approximately 10 mL/3.0 mmol) and ethyl acetate (EtOAc) (approximately 20 mL/3.0 mmol) to remove organic by-products and unreacted starting materials. The aqueous layer is separated and solvents are subsequently lyophilized off after freezing the solution to afford the crude (4-acetamidophenoxy) carbamates or -thiocarbonates which can be used directly in subsequent reaction steps or can be further purified by any methods known in the art including preparative RP-HPLC or crystallization.

Example 1

Synthesis of 4-Acetamidophenyl 4-nitrophenyl carbonate (3)

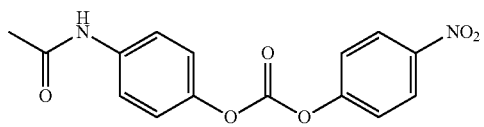 [SMILES: CC(=O)Nc1ccc(OC(=O)Oc2ccc([N+](=O)[O-])cc2)cc1]

Adapting a known procedure (P. Pasetto, et al., *Anal. Chim. Acta*, 2005, 542(1), 66-75), 8.03 mL of anhydrous pyridine (7.84 g, 99.3 mmol; 1.5 eq.) was added at a temperature of about 0° C. (ice bath) to a suspension of 10.00 g N-(4-hydroxyphenyl)acetamide (1) (paracetamol (INN), acetaminophen (USAN) (66.2 mmol; 1.0 eq.) in 300 mL of anhydrous dichloromethane (DCM). The reaction mixture was stirred at the same temperature for about 10 minutes. To this mixture, a solution of 13.97 g (69.5 mmol; 1.05 eq.) of commercially available 4-nitrophenyl carbonochloridate (2) in 20 mL of anhydrous DCM was then added dropwise and the reaction mixture was stirred with gradual warming to room temperature for overnight. Fifty (50) mL of water were added to the reaction mixture. A solid precipitated out of solution. The solid was filtered off and washed successively with diethyl-ether (Et$_2$O) (2×50 mL) and hexane (4×50 mL) to afford 9.92 g (47% yield) of the target compound 3 as a colorless solid after drying in high vacuum. The initial filtrate (DCM and water) was washed with a saturated aqueous solution of sodium chloride (NaCl/brine). The organic layer was dried using anhydrous sodium sulfate (Na$_2$SO$_4$) to afford an additional 7.0 g (33% yield) of the target compound 3. R$_f$-value: 0.35 (ethyl acetate/hexane=1:1). $^1$H NMR (DMSO-d$^6$, 300 MHz): δ=10.09 (s, 1H), 8.34 (d, J=9.3 Hz, 2H), 7.68 (d, J=9.3 Hz, 2H), 7.64 (d, J=9.0 Hz, 2H), 7.31 (d, J=8.7 Hz, 2H), 2.05 (s, 3H) ppm. LC/MS (ESI): m/z=317.2 [M+H]$^+$. The analytical data corresponded to the analytical data given in the literature.

Example 2

Synthesis of Sodium 2-aminoethanesulfinate (5)

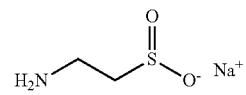

Sodium 2-aminoethanesulfinate (5) was prepared according to the General Procedure for the Preparation of Alkali Metal Salts (Procedure A). 2-Aminoethanesulfinic acid (hypotaurine) (4) (350 mg, 3.21 mmol) was dissolved in 2 mL of degassed water and reacted with 3.21 mL (3.21 mmol) of a 1.0 N aqueous sodium hydroxide solution (NaOH$_{(aq.)}$) (1.0 eq.). The reaction mixture was degassed through repetitive vacuum/nitrogen purge cycles and was heated to about 55° C. for about 30 minutes. The reaction mixture was frozen and the solvent was removed through lyophilization to yield 410 mg (97% yield) of the target material 5 as a colorless solid. $^1$H NMR (300 MHz, D$_2$O): δ 2.75 (t, J=6.6 Hz, 2H), 2.29 (t, J=6.9 Hz, 2H) ppm. The analytical data corresponded to the analytical data given in the literature and the proposed structure.

Example 3

Synthesis of Sodium 2-aminoethanesulfonate (7)

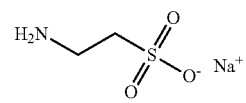

Sodium 2-aminoethanesulfonate (7) is commercially available and was also prepared according to the General Procedure for the Preparation of Alkali Metal Salts (Procedure A). 2-Aminoethanesulfonic acid (taurine) (6) (1.0 g, 8.0 mmol) was dissolved in 8 mL of water and was reacted with 320 mg (8.0 mmol; 1.0 eq.) of solid sodium hydroxide (NaOH) at 60° C. with sonication. The reaction mixture was frozen and the solvent was removed through lyophilization to yield 1.0 g (~quantitative yield) of the target compound 7 as a colorless solid. $^1$H NMR (300 MHz, D$_2$O): δ 2.90-2.80 (m, 4H) ppm. The analytical data corresponded to the analytical data given in the literature and the proposed structure.

Example 4

Synthesis of Disodium (2R)-2-amino-3-sulfonato-propanoate (9)

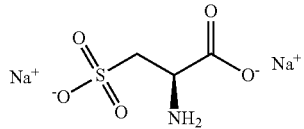

Disodium (2R)-2-amino-3-sulfonato-propanoate (9) was prepared according to the General Procedure for the Preparation of Alkali Metal Salts (Procedure A). Five hundred (500) mg (2.67 mmol) of (2R)-2-amino-3-sulfo-propanoic acid monohydrate (8) (cysteine sulfonic acid mono hydrate) were dissolved in 2 mL of water. The disodium salt was formed through reaction with 5.34 mL (5.34 mmol; 2.0 eq.) mmol) of a 1.0 N aqueous sodium hydroxide solution (NaOH$_{(aq.)}$). The mixture was heated to about 55° C. for about one (1) hour to ensure complete salt formation. The reaction mixture was frozen and the solvent was removed through lyophilization to yield 550 mg (~quantitative yield) of the target compound 9 as a colorless solid. $^1$H NMR (300 MHz, D$_2$O): δ 4.12 (dd, J=9.3, 3.0 Hz, 1H), 3.37 (dd, J=15.0, 3.0 Hz, 1H), 3.19 (dd, J=15.0, 9.3 Hz, 1H) ppm. The analytical data corresponded to the analytical data given in the literature and the proposed structure.

Example 5A

Synthesis of crude 2-((4-Acetamidophenoxy)carbonylamino)ethanesulfinic acid (11a) (formula (II)

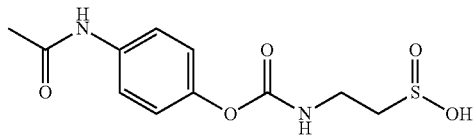 [SMILES: CC(=O)Nc1ccc(OC(=O)NCCS(=O)O)cc1]

Title compound 11a was prepared according to the General Method for the Reaction of Alkali Metal Salts of Amino Acid Derivatives with 4-Acetamidophenyl 4-Nitrophenyl Carbonate (3). A solution of 410 mg (3.20 mmol) of sodium 2-aminoethanesulfinate (5) in approximately one (1) mL of degassed water was reacted with a solution of 4-acetamidophenyl 4-nitrophenyl carbonate (3) (1.01 g, 3.19 mmol) in 10 mL of acetonitrile (MeCN). After work-up procedures, the aqueous layer was lyophilized off to afford 910 mg (~quantitative yield) of the crude 2-((4-acetamidophenoxy)carbonylamino)ethanesulfinic acid (11a) which was used directly and without further isolation or purification procedures in the next step. The material thus obtained was contaminated with some sodium chloride (NaCl) and/or other sodium salts. $^1$H NMR (300 MHz, D$_2$O): δ 7.22 (d, J=9.0 Hz, 2H), 6.93 (d, J=9.0 Hz, 2H), 3.31 (t, J=6.6 Hz, 2H), 2.42 (t, J=6.6 Hz, 2H), 1.96 (s, 3H). LC/MS (ESI): m/z=287.1 [M+H]$^+$.

Example 5B

Synthesis of Purified 2-((4-Acetamidophenoxy)carbonylamino)ethanesulfinic acid (11a)

A sample (300 mg) of the 2-((4-acetamidophenoxy)carbonylamino)ethanesulfinic acid (11a) prepared by comparative methods as described above was purified by preparative HPLC using a gradient consisting of acetonitrile and water containing 0.1 vol-% of formic acid. A sample eluting at 2% acetonitrile and 98% water was collected to afford 193 mg (64% recovery) of the title compound (11a) as a colorless solid after lyophilization of the solvent. The solid was shown by analytical HPLC and LC/MS to consist of a mixture of the title compound (11a) (75%) plus the corresponding oxidized product (25%), 2-((4-acetamidophenoxy)carbonylamino) ethanesulfonic acid (12a). 2-((4-Acetamidophenoxy)carbonylamino)ethanesulfinic acid (11a): R$_t$=6.943 min; LC/MS (ESI): m/z=287.1 [M+H]$^+$. 2-((4-Acetamidophenoxy)carbonylamino)ethanesulfonic acid (12a): R$_t$=5.043 min; LC/MS (ESI): m/z=0.0 303.0 [M+H]$^+$.

Example 6

Synthesis of Sodium 2-((4-acetamidophenoxy)carbonylamino)ethanesulfinate (11) (formula (IIa)

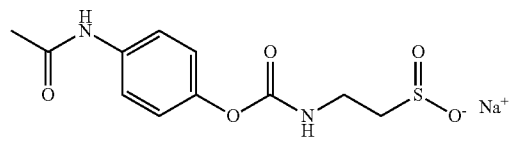 [SMILES: CC(=O)Nc1ccc(OC(=O)NCCS(=O)[O-])cc1 ; [Na+]]

Sodium 2-((4-Acetamidophenoxy)carbonylamino) ethanesulfinic acid 11 was prepared following the General Procedure for the Preparation of Alkali Metal Salts (Procedure B). 2-((4-Acetamidophenoxy)carbonylamino)ethanesulfinic acid (11a) (910 mg, 3.18 mmol, 1.0 eq.), dissolved in 3 mL of degassed water, was reacted with 267.3 mg (3.18 mmol; 1.0 eq.) of sodium hydrogencarbonate (NaHCO$_3$) dissolved in 5 mL of degassed water. The mixture was frozen and the solvents lyophilized off to afford 950 mg (96%) of the title compound (II) as an off-white solid. The material thus obtained was contaminated with some sodium chloride (NaCl) and other sodium salts. R$_t$=6.91 min; $^1$H NMR (300 MHz, D$_2$O): δ 7.20 (d, J=8.7 Hz, 2H), 6.92 (d, J=8.7 Hz, 2H), 3.28 (t, J=6.3 Hz, 2H), 2.39 (t, J=6.3 Hz, 2H), 1.95 (s, 3H). LC/MS (ESI): m/z=287.1 [M+H]$^+$, 309.1 [M+Na]$^+$.

Example 7A

Synthesis of Crude 2-((4-Acetamidophenoxy)carbonylamino)ethanesulfonic acid (12a)

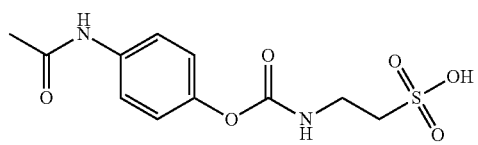 [SMILES: CC(=O)Nc1ccc(OC(=O)NCCS(=O)(=O)O)cc1]

((4-Acetamidophenoxy)carbonylamino)ethanesulfonic acid (12a) was prepared according to the General Method for the Reaction of Alkali Metal Salts of Amino Acid Derivatives with 4-Acetamidophenyl 4-Nitrophenyl carbonate (3). A solution of 511 mg (3.48 mmol) of sodium 2-aminoethanesulfonate (7) in approximately one (1) mL of degassed water was reacted with a solution of 4-acetamidophenyl 4-nitrophenyl carbonate (3) (1.10 g, 3.48 mmol) dissolved in 5 mL of acetonitrile (MeCN). After work-up procedures, the aqueous layer was lyophilized off to afford 1.0 g (~quantitative yield) of the crude 2-((4-acetamidophenoxy)carbonylamino) ethanesulfonic acid (12a) which was used directly and without further isolation or purification procedures. The material thus obtained was contaminated with some sodium chloride (NaCl) and other sodium salts. $^1$H NMR (300 MHz, D$_2$O): δ 7.22 (d, J=9.0 Hz, 2H), 6.94 (d, J=8.7 Hz, 2H), 3.40 (t, J=6.6 Hz, 2H), 2.95 (t, J=6.6 Hz, 2H), 1.96 (s, 3H). LC/MS (ESI): m/z=303.0 [M+H]$^+$, 602.8 [2M−H]$^−$.

Example 7B

Synthesis of Purified 2-((4-Acetamidophenoxy)carbonylamino)ethanesulfonic acid (12a)

A sample (150 mg) of the 2-((4-acetamidophenoxy)carbonylamino)ethanesulfonic acid 12a prepared by comparative methods as described above was purified by preparative HPLC using a gradient consisting of acetonitrile and water containing 0.1 vol-% of formic acid. Samples eluting at a gradient from 2% acetonitrile 98% water to 20% acetonitrile/80% water were collected, pooled, and lyophilized to afford 78.2 mg (52% recovery) of the title compound (12a) as a colorless solid.

Example 8

Synthesis of Sodium 2-((4-acetamidophenoxy)carbonylamino)ethanesulfonate (12)

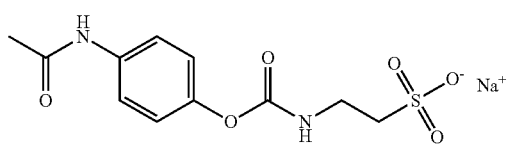 [SMILES: CC(=O)Nc1ccc(OC(=O)NCCS(=O)(=O)[O-])cc1 ; [Na+]]

Sodium 2-((4-Acetamidophenoxy)carbonylamino) ethanesulfonic acid (12) was prepared following the General Procedure for the Preparation of Alkali Metal Salts (Procedure B). 4-Acetamidophenoxy)carbonylamino)ethanesulfonic acid (12a) (1.0 g, 3.3 mmol), dissolved in 5 mL of water, was reacted with 275 mg (3.27 mmol; 1.0 eq.) of sodium hydrogencarbonate (NaHCO$_3$) dissolved in 2 mL of water. The mixture was frozen and the solvents lyophilized off to afford 1.10 g (~quantitative yield) of the title compound (12) as a colorless solid. The material thus obtained was contaminated with some sodium chloride (NaCl) and other sodium salts. R$_f$=5.024 min. $^1$H NMR (300 MHz, D$_2$O): δ=7.25 (d, J=9.0 Hz, 2H), 6.97 (d, J=8.7 Hz, 2H), 3.43 (t, J=6.6 Hz, 2H), 2.98 (t, J=6.9 Hz, 2H), 2.00 (s, 3H). LC/MS (ESI): m/z=303.0 [M+H]$^+$, 626.8 [2M+Na]$^+$, 602.8 [2M−H]$^−$.

Example 9A

Synthesis of (2R)-2-[(4-Acetamidophenoxy)carbonylamino]-3-sulfo-propanoic acid (13a)

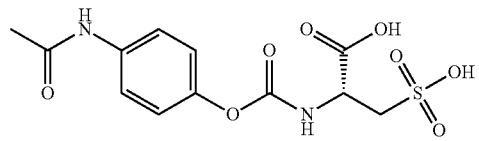 [SMILES: CC(=O)Nc1ccc(OC(=O)N[C@@H](CS(=O)(=O)O)C(=O)O)cc1]

(2R)-2-[(4-Acetamidophenoxy)carbonylamino]-3-sulfo-propanoic acid (13a) was prepared according to the General Method for the Reaction of Alkali Metal Salts of Amino Acid Derivatives with 4-Acetamidophenyl 4-Nitrophenyl Carbonate (3). A solution of 500 mg (2.35 mmol) of disodium (2R)-2-amino-3-sulfonato-propanoate (9) in approximately one (1) mL of water was reacted with a solution of 4-acetamidophenyl 4-nitrophenyl carbonate (3) (844 mg, 2.67 mmol) dissolved in 5 mL of acetonitrile (MeCN). The mixture was heated to about 55° C. for two (2) hours. After work-up procedures, the aqueous layer was lyophilized off to afford 400 mg (43% yield) of the crude 2-[(4-acetamidophenoxy)carbonylamino]-3-sulfo-propanoic acid (13a). The material thus obtained was contaminated with some sodium chloride (NaCl) and other sodium salts. The crude product was further purified by preparative HPLC using a gradient consisting of acetonitrile and water containing 0.1 vol-% of formic acid. Samples eluting at 2% acetonitrile and 98% water were collected, frozen, and lyophilized off to afford 83 mg (9% yield) the target compound (13a) as a colorless solid. R$_f$=3.10 min. $^1$H NMR (300 MHz, D$_2$O): δ=7.25 (d, J=9.0 Hz, 2H), 6.99 (d, J=9.0 Hz, 2H), 4.54-4.50 (m, 1H), 3.32-3.27 (m, 2H), 1.98 (s, 3H). LC/MS (ESI): m/z=347.0 [M+H]$^+$, 714.8 [2M+Na]$^+$.

Example 10

Synthesis of Disodium (2R)-2-((4-acetamidophenoxy)carbonylamino)-3-sulfonatopropanoate (13)

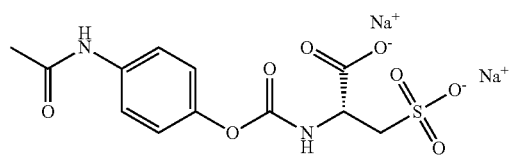 [SMILES: [Na+] ; CC(=O)Nc1ccc(OC(=O)N[C@@H](CS(=O)(=O)[O-])C(=O)[O-])cc1 ; [Na+]]

Disodium (2R)-2-((4-acetamidophenoxy)carbonylamino)-3-sulfonatopropanoate (13) was prepared following the General Procedure for the Preparation of Alkali Metal Salts (Procedure B). (2R)-2-[(4-Acetamidophenoxy)carbonylamino]-3-sulfo-propanoic acid (13a) (83 mg, 0.24 mmol), dissolved in 2.0 mL of water, was reacted with 40.3 mg (0.48 mmol; 2.0 eq.) of sodium hydrogencarbonate (NaHCO$_3$) dissolved in 0.5 mL of water. The mixture was sonicated with agitation for three (3) minutes, frozen, and the solvents lyophilized off to afford 88 mg (95% yield) of the title compound (13) as a colorless solid. $^1$H NMR (300 MHz, D$_2$O): δ=7.21 (d, J=8.7, 2H), 6.97 (d, J=9.0, 2H), 4.36-4.32 (m, 1H), 3.28-3.22 (m, 1H), 3.12-3.04 (m, 1H), 1.96 (s, 3H) ppm. LC/MS: LC/MS (ESI): m/z=347.0 [M+H]$^+$, 714.7 [2M+Na]$^+$.

Example 11

Synthesis of Sodium 2-((4-acetamidophenoxy)carbonylthio)ethanesulfonate (14; Formula (Ia))

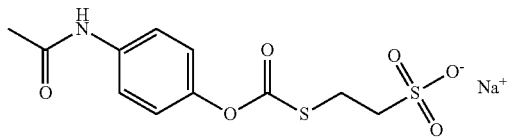 [SMILES: CC(=O)Nc1ccc(OC(=O)SCCS(=O)(=O)[O-])cc1 ; [Na+]]

Sodium 2-((4-acetamidophenoxy)carbonylthio)ethanesulfonic acid (14) was prepared by adapting the General Method for the Reaction of Alkali Metal Salts of Amino Acid Derivatives with 4-Acetamidophenyl 4-Nitrophenyl carbonate (3) to install the thiocarbonate functionality. Under a nitrogen atmosphere and at room temperature, a solution of 4.94 g (30.1 mmol) of commercially available sodium-2-mercaptoethane sulfonate (10) ($^1$H NMR (300 MHz, D$_2$O): δ 2.98 (t, J=7.2 Hz, 2H), 2.67 (t, J=7.2 Hz, 2H) ppm) in approximately 25 mL of degassed water was drop-wise added to a solution of 4-acetamidophenyl 4-nitrophenyl carbonate (3) (9.92 g, 31.4 mmol) in 300 mL of acetonitrile (MeCN). Solid sodium hydrogencarbonate (NaHCO$_3$) (1.15 g, 13.7 mmol was subsequently added in small portions over 30 minutes. The reaction mixture turned turbid (white) and after about 45 minutes it turned green. The reaction course was followed by analytical LC/MS. The reaction was stirred overnight at room temperature. Upon completion of the reaction, the reaction mixture was diluted with dichloromethane (DCM) (175 mL) and water (25 mL) where upon the reaction mixture turned clear. The resulting two layers were separated and the organic layer containing some of the targeted product (14), unreacted 4-acetamidophenyl-4-nitrophenyl carbonate (3), and by-products bis(4-acetamidophenyl) carbonate (dimer carbonate), 4-nitrophenol, and N-(4-hydroxyphenyl)acetamide (1) was discarded. The aqueous layer which contained the desired product was concentrated to dryness under reduced pressure using a rotary evaporator. Acetonitrile (MeCN) (100 mL) was added to the green residue whereupon a solid was formed. The solid was filtered off using a Büchner-funnel and the resulting filter residue was subsequently washed with diethylether (Et$_2$O) (2×25 mL) and with hexanes (3×20 mL). The solid obtained was dried in high vacuum to afford 7.84 g (82% yield) the target compound (14) as yellow solid (99% purity by analytical HPLC). The yellow solid was suspended in a mixture of isopropyl alcohol (iPrOH, IPA)/Ethyl acetate (EtOAc) (400 mL; 1:2 v/v) containing distilled water (20 mL). The supernatant was decanted and the remaining solid was again treated with iPrOH/EtOAc (300 mL; 1:2 v/v) containing distilled water (25 mL). The layers were separated and the aqueous layer was extracted with iPrOH/EtOAc (200 mL; 1:2 v/v). The combined organic solvents were removed under reduced pressure using a rotary evaporator to furnish 2.5 g (25% yield) of the target product (14) as a pale yellow solid. The aqueous layer was concentrated to dryness under reduced pressure using a rotary evaporator and at about 50° C. to afford another 4.2 g (41% yield) of product (14). Absolute ethanol (EtOH) (10 mL) was added to the batch of compound (14) obtained from the organic extracts (2.5 g) followed by slow addition of distilled water (3 mL) while heating the flask to about 55° C. until a clear solution formed. The solution was allowed to cool for about two (2) hours during which time the target compound (14) crystallized out. The crystals were filtered off using a Büchner-funnel and the resulting filter residue was subsequently washed with EtOH (2×5 mL), diethyl ether (2×20 mL) and hexanes (3×20 mL) to afford 1.6 g (16% yield) of thiocarbonate (14) as colorless crystals after drying in high vacuum. To further remove chloride traces (positive AgNO$_3$ test), the crystals were washed with a cold mixture of ethanol (EtOH)/water (9:1 v/v; 20 mL) and dried under reduced pressure to afford 995 mg (10% yield) of the title compound (14) as colorless crystals. Analytical RP-HPLC: 100% purity. R$_t$=8.62 min. $^1$H NMR (300 MHz, D$_2$O): δ 7.24 (d, J=9.0 Hz, 2H), 6.99 (d, J=9.0 Hz, 2H), 3.08-3.00 (m, 4H), 1.96 (s, 3H) ppm. LC/MS (ESI): m/z=660.8 [2M+Na]$^+$.

Example 12

Crystallization of Sodium 2-((4-acetamidophenoxy)carbonylthio)ethanesulfonate (14; Formula (Ia))

A sample recovered from the aqueous phase of different reaction batches in the synthesis of compound (14) was purified by crystallization. 1.4 g of crude sodium 2-((4-acetamidophenoxy)carbonylthio)ethanesulfonate (14) was heated in a mixture of absolute ethanol (EtOH) and distilled water (10 mL/3.5 mL) to about 55° C. to form a clear solution. Upon cooling to room temperature, colorless crystals began to form after about 15 minutes. Crystallization was allowed to complete for an additional three (3) to four (4) hours at room temperature. The crystals were filtered off, washed with four (4) mL of a cold mixture of EtOH/water (9:1 v/v), and dried in high vacuum to afford 529 mg (38% recovery) of the target compound (14). Analytical RP-HPLC: 100% purity. R$_t$=9.21 min. The other analytical data are identical to the data given in Example 11.

Example 13

Test Article Pharmacokinetics

Forty-eight (48) male and female Sprague-Dawley rats were assigned to eight dose groups consisting of three animals per test article per dose route per gender. There were four test articles including acetaminophen, obtained from Sigma-Aldrich, and three acetaminophen conjugates as set forth below.

| Test Article | Compound Identifier | Chemical Structure |
| --- | --- | --- |
| Acetaminophen | APAP | 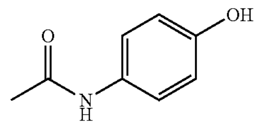 |
| Sodium 2-((4-acetamidophenoxy)carbonylthio)ethanesulfonate | Compound 14; Formula (Ia); Test Article A | 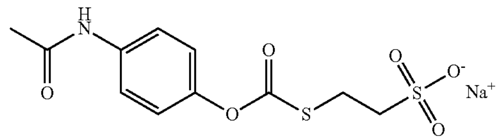 [SMILES: CC(=O)Nc1ccc(OC(=O)SCCS(=O)(=O)[O-])cc1 ; [Na+]] |
| sodium (((4-acetamidophenoxy)carbonyl)amino)methanesulfinic acid | Compound 11; Formula (IIa); Test Article B | 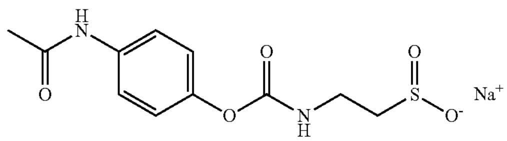 [SMILES: CC(=O)Nc1ccc(OC(=O)NCCS(=O)[O-])cc1 ; [Na+]] |
| sodium (((4-acetamidophenoxy)carbonyl)amino)methanesulfonic acid | Compound 12; Test Article C | 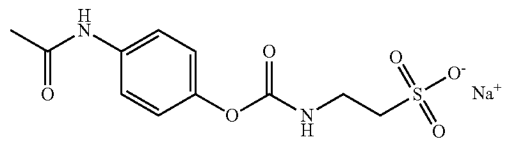 [SMILES: CC(=O)Nc1ccc(OC(=O)NCCS(=O)(=O)[O-])cc1 ; [Na+]] |

The animals received a single dose (oral or intravenous) of the test articles via oral gavage or slow intravenous bolus. Dose concentrations of the acetaminophen conjugates were adjusted to provide a weight-adjusted acetaminophen dose comparable to the acetaminophen oral (10 mg/kg) and intravenous (3 mg/kg) doses. Cage-side observations were performed daily; body weights were recorded prior to each dosing day. Blood samples for pharmacokinetic (PK) analyses were collected at 5 minutes to 8 hr post-dose and acetaminophen plasma concentrations were measured via a LC-MS/MS method.

All test articles were well tolerated when administered as a single oral or intravenous dose to male and female rats. There was no mortality nor abnormal clinical observations noted during this study.

Figure 1B:
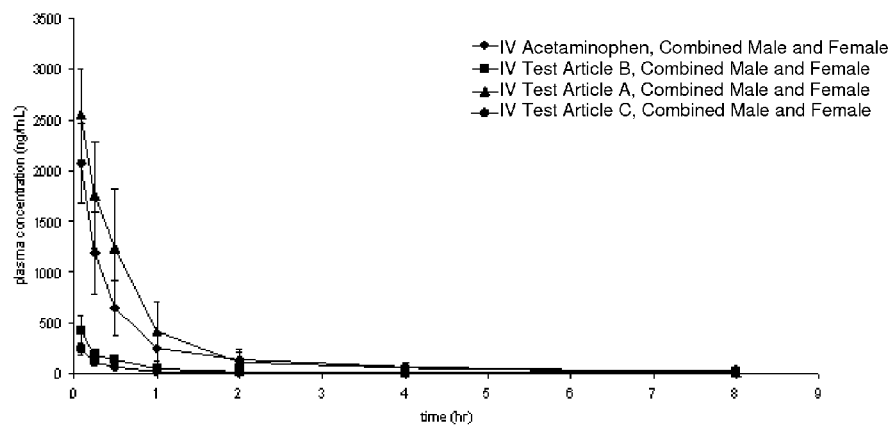
FIG. 1B illustrates the plasma acetaminophen concentration versus time curve for acetaminophen and Test Articles A, B and C following intravenous administration to rats.

Acetaminophen was present in plasma after oral and intravenous administration of acetaminophen and the acetaminophen conjugates (Test Articles A, B and C). Plasma concentrations of the parent drugs, i.e., Test Articles A, B, and C were not measured in this study. Acetaminophen exposures were relatively consistent across individual animals, with the greatest variability in acetaminophen concentrations seen after oral administration in animals treated with Test Article C. As illustrated in FIGS. 1A and 1B, plasma acetaminophen concentration versus time curves were relatively well-behaved, with defined absorption and elimination phases after oral administration and an elimination phase after intravenous administration.

FIGS. 1A and 1B also illustrate that Test Article A exhibited greater plasma concentrations with time (up to 4 hours) than did Test Articles B and C, after both oral and intravenous administration. After oral administration, Test Article A also exhibited greater plasma concentrations with time after hour 1 as compared to acetaminophen. After intravenous administration, Test Article A also exhibited greater plasma concentration with time up to hour 1 as compared to acetaminophen.

Non-compartmental pharmacokinetic analysis was conducted for mean plasma acetaminophen concentrations for each test article. Measures of acetaminophen exposure (e.g., $AUC_{last}$) were typically greater in female animals than male animals for all test articles and for both the oral and intravenous routes of administration.

Test Article A behaved somewhat differently from Test Article C and Test Article B in both male and female animals. As illustrated in FIG. 2B, Test Article A was observed to have greater plasma acetaminophen concentrations after intravenous administration compared to Test Article C and Test Article B. After oral administration, Test Article A was also observed to exhibit greater acetaminophen plasma concentrations and to have a longer time to maximum acetaminophen plasma concentrations than Test Article C and Test Article B, as illustrated in FIG. 2A. Relative exposures to acetaminophen for Test Article C and Test Article B were 23.1% to 53.2% compared to oral acetaminophen. In contrast, relative exposures to acetaminophen for Test Article A were in the 104.8% to 134.4% range compared to oral acetaminophen. A similar pattern was apparent after intravenous administration, where relative exposures to acetaminophen for Test Article C and Test Article B were in the 15.1% to 20.6% range, but for Test Article A these exposures were in the 124.2% to 148.2% range.

Further pharmacokinetic details are provided in FIGS. 2A and 2B. These data show a more rapid exposure to acetaminophen following intravenous administration. Importantly for Test Article A, the oral AUC, which is an indicator of total exposure to acetaminophen, is 3,737, which on average is about 120% of the 3,313 value provided by unmodified acetaminophen. Following intravenous administration, the AUC is 1,937, which on average is about 132% of the 1,467 value provided by unmodified acetaminophen. The data in FIG. 2 show that Test Article A outperforms Test Articles B and C in those parameters, which suggest higher exposure.

In summary, the plasma pharmacokinetics of oral and intravenous acetaminophen and the acetaminophen conjugates Test Articles A, B, and C were defined in male and female Sprague Dawley rats. When dosed at equivalent acetaminophen doses, Test Article B and Test Article C produced acetaminophen exposures that were substantially lower than obtained after administration of acetaminophen. In contrast, Test Article A produced acetaminophen exposures that were as great as, or greater than, comparable exposures after acetaminophen administration.

Example 14

Hydrolysis and Metabolism of Test Articles in Human and Rat Whole Blood

The appearance of acetaminophen (APAP) when Test Articles A, B and C are incubated in human and rat whole blood at 37° C. was determined. Loss of deuterated acetaminophen (APAP-d4) was also monitored in order to account for compound losses due to the metabolism of acetaminophen. Stability of the test samples in PBS at 37° C. was also determined.

Sample Preparation

Five lots of human whole blood (lithium heparin) were purchased from Biochemed and stored refrigerated at +5° C.±3° C. until use. Five lots of SD Rat whole blood (lithium heparin) were purchased from Biochemed and stored refrigerated at +5° C.±3° C. until use. Phosphate-buffered saline was used as a control matrix; it was prepared in-house and stored refrigerated at +5° C.±3° C. until use. Test Articles were weighed immediately prior use.

Test Articles A, B and C were weighed on a microbalance and dissolved in water to generate individual stock solutions, each at a concentration of 3.31 mM. Purity was taken into account for each stock solution prepared. APAP-d4 was weighed on a microbalance and dissolved in water to generate a stock solution at a 3.31 mM concentration. Purity was taken into account for the stock preparation. One part Test Article A, B or C and one part APAP-d4 was added to three parts water to arrive at an intermediate solution consisting of 662 µM for each compound.

Human Whole Blood Incubation and Sampling

Whole blood was removed from storage and allowed to reach room temperature. It was pooled by species at this time. Once the pool reached room temperature, individual 1980 µL aliquots of the whole blood pool were added to the appropriate tubes on test. All tubes were pre-incubated at 37° C. in a water bath for 5 minutes.

The appropriate intermediate solution was added to each tube on test such that the final concentration of the test article in blood was 6.62 µM. The compound was assayed in triplicate at this concentration. Nominal 0-minute samples were aliquoted into a 96-well plate as soon as spiking solution was added. Just prior to a 150 µL sample transfer, 300 µL of acetonitrile:methanol (1:1) was placed in the individual receiving wells in order to stop conversion reactions. The plate containing "stopped" samples was held, covered, in a wet-ice bath until all remaining timepoints were aliquoted. All remaining spiked samples were incubated at 37° C. in a water bath throughout the sampling period. At 2.5, 5, 10, 30, 60, 120, and 240 minutes, a 150 µL aliquot of each spiked sample was removed and transferred into the 96-well plate. Just prior to each transfer, 300 µL of acetonitrile:methanol (1:1) was placed in the receiving wells for those aliquots in order to stop conversion reactions. Once all samples were collected, the plate was vortexed gently and centrifuged to pellet the precipitated proteins, and the resultant supernatants transferred to a fresh 96-well plate for extraction and analysis.

Rat Whole Blood and PBS Incubation and Sampling

Whole blood was removed from storage and allowed to reach room temperature. It was pooled by species at this time. Once the pool reached room temperature, individual 1,980 µL aliquots of the whole blood pool were added to the appropriate tubes on test. Individual 1,980 µL aliquots of blank phosphate buffered saline (PBS) were added to the appropriate tubes on test. All tubes were pre-incubated at 37° C. in a water bath for 5 minutes.

The appropriate intermediate solution was added to each tube on test such that the final concentration of the test article in blood was 6.62 µM. The compound was assayed in triplicate at this concentration. Nominal 0-minute samples were aliquoted into a 96-well plate as soon as spiking solution was added. Just prior to a 150 µL sample transfer, 450 µL of acetonitrile:methanol (1:1) was placed in the individual receiving wells in order to stop conversion reactions. The plate containing "stopped" samples was held, covered, in a wet-ice bath until all remaining timepoints were aliquoted. All remaining spiked samples were incubated at 37° C. in a water bath throughout the sampling period. At 2.5, 5, 10, 30, 60, 120, and 240 minutes, a 150 µL aliquot of each spiked sample was removed and transferred into the 96-well plate. Just prior to each transfer, 450 µL, of acetonitrile:methanol (1:1) was placed in the receiving wells for those aliquots in order to stop conversion reactions. Once all samples were collected, the plate was vortexed gently and centrifuged to pellet the precipitated proteins, and the resultant supernatants transferred to a fresh 96-well plate for extraction and analysis. Samples were analyzed for acetaminophen and acetaminophen-d4 concentrations, using methods that employ HPLC and MS/MS detection; the results are shown in FIG. 3.

Summary of Results

Figure 3A:
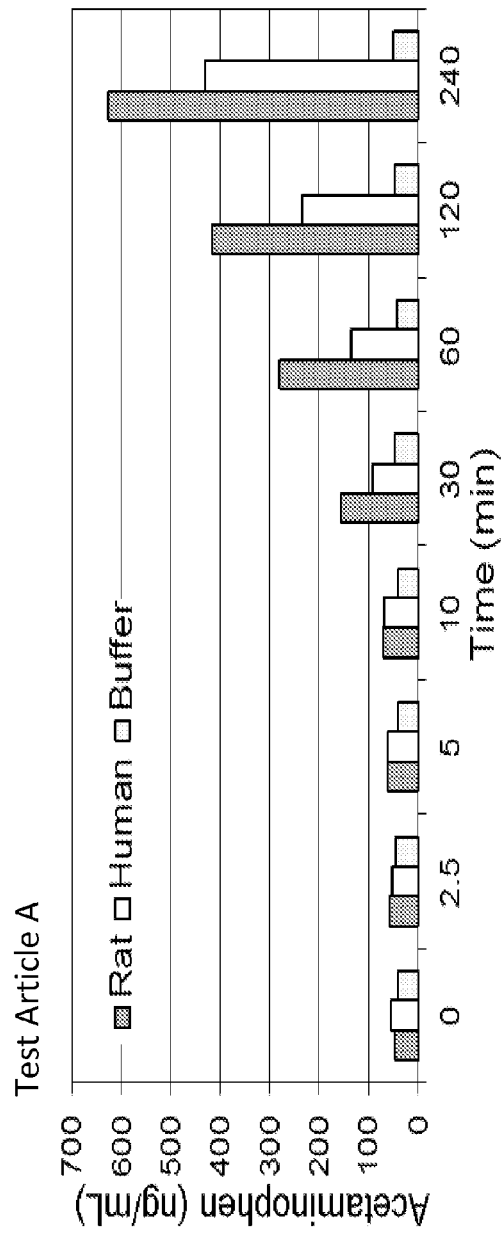
FIGS. 3A, 3B and 3C illustrate acetaminophen concentration (μg/mL) with time upon incubation of Test Articles A, B and C, respectively, in human whole blood, rat whole blood and PBS.

For Test Article A, as shown in FIG. 3A, conversion to acetaminophen was observed in both rat and human whole blood incubations, with concentrations of 628 and 431 ng/mL at 4 hours in rat and human plasma, respectively. Rat whole blood converts Test Article A to APAP to a greater degree and more rapidly than human whole blood. Test Article A also appears to be rather stable in PBS at 37° C. out to four hours.

Figure 3B:
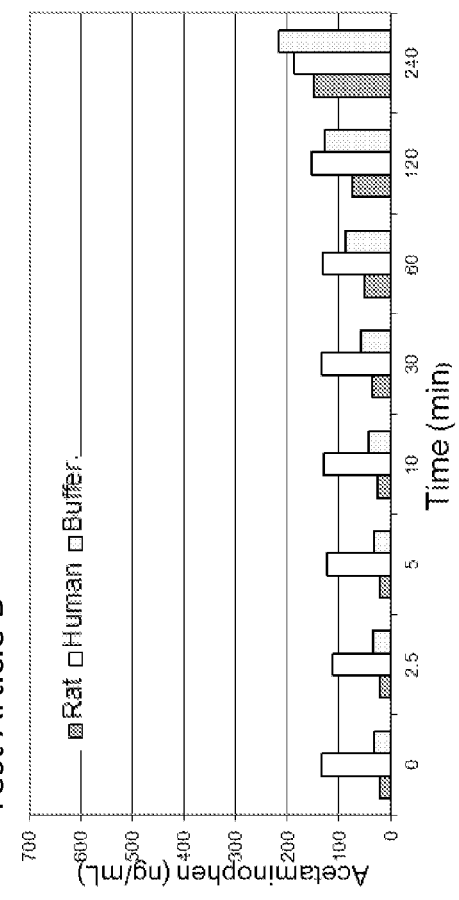
Figure 3C:
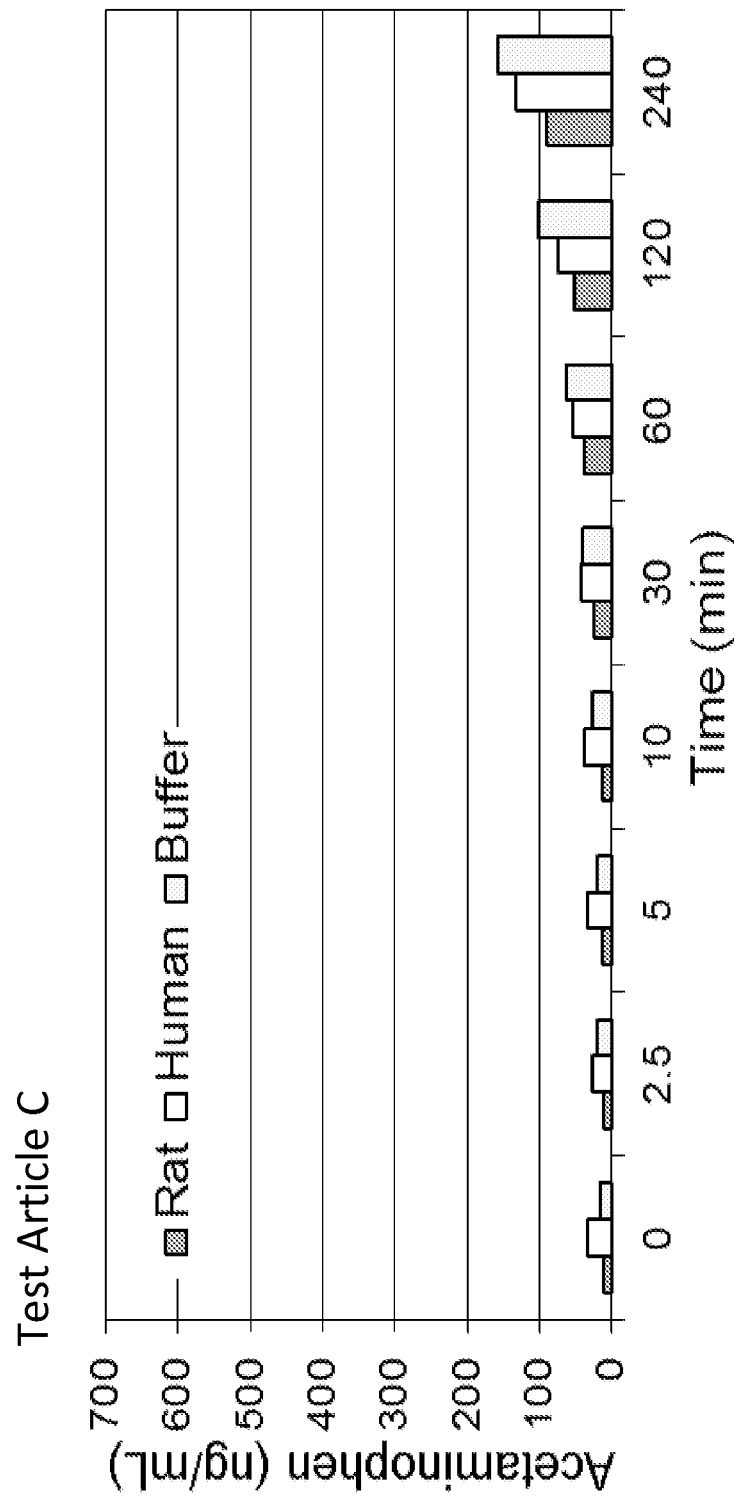

For Test Article B, which is shown in FIG. 3B, conversion to APAP was observed in all incubations. However, conversion is nearly equivalent in blood incubations and buffer incubations, suggesting that Test Article B is not stable in PBS at 37° C. alone. Therefore, it appears that most of the conversion seen in all incubations was non-enzyme related.

For Test Article C (FIG. 3C), conversion to APAP was observed in all incubations. However, conversion is nearly equivalent in blood incubations and buffer incubations, suggesting that Test Article C is not stable in PBS at 37° C. alone. As is the case for Test Article B, it appears that most of the conversion seen in all incubations is non-enzyme related.

These data suggest that Test Article A is more readily and rapidly converted to acetaminophen than either Test Articles B or C. In addition, Test Article A was stable in PBS at 37° C. out to four hours, which suggests that Test Article A may be readily prepared in a saline solution without imminent loss of activity or degradation, which may be important for the potential to prepackage stable injection solutions or for the ability to reconstitute the compound prior to clinical use. The stability of APAP-d4 in all incubations suggests that concentration values have not been altered significantly by subsequent metabolism of released acetaminophen.

Example 15

Rat Liver Microsome-Mediated Metabolism

The appearance of acetaminophen (APAP) when Test Articles A, B and C are incubated in rat liver microsomes at 37° C. was determined. Loss of APAP-d4 was also monitored.

Sample Preparation

Two lots of rat liver microsomes were purchased from BD Biosciences and stored frozen at −80° C. until use. Lot 62548 consisting of ~334 male rat livers and lot 59232 consisting of 10 female rat livers were pooled at a 1:1 ratio just before use. Test Articlea A, B, and C were weighed on a microbalance and dissolved in water to generate individual stock solutions, each at a concentration of 3.31 mM. Purity was taken into account for each stock solution prepared. Compounds were weighed immediately prior to use. APAP-d4 was weighed on a microbalance and dissolved in water to generate a stock solution at a 3.31 mM concentration. Purity was taken into account for the stock preparation. One part Test Article A, B or C and one part APAP-d4 was added to three parts water to arrive at an intermediate solution consisting of 662 µM for each compound.

Incubation and Sampling

The intermediate solutions prepared above were added to phosphate buffer to arrive at solutions consisting of 8.827 µM of each compound; these were called Substrate solutions. Incubation wells were placed in a wet ice-bath. 750 µL of Substrate solution was added to the appropriate wells. 750 µL of 100 mM Potassium phosphate was added to wells that did not get Substrate solution. 50 µL of Microsomal suspension (20 mg/mL) was added to the appropriate wells. 50 µL of 100 mM Potassium phosphate buffer, pH 7.4 was added to the appropriate wells that did not receive microsomes. Samples were pre-incubated by shaking at 37° C. for 5 minutes. Just prior to starting the reactions in the next step 80 µL aliquots were removed and "killed" with 200 µL of Stop Solution; these were the 0 min samples. Reactions for the remaining samples were started by adding 180 µL Cofactor Solution (5×) to the appropriate wells. A 180 µL aliquot of 2% sodium bicarbonate in purified water was added to the incubation samples that did not receive cofactor. A 20 µL aliquot of Cofactor Solution (5×) was added to the stopped 0 min samples. A 20 µL aliquot of 2% sodium bicarbonate in purified water was added to the stopped 0 min samples that did not receive cofactor. At 2.5, 5, 10, 30, 60, 120, and 240 minutes, 100 µL of the specified incubation sample was removed and "killed" with 200 µL of Stop solution. Once all required samples were collected, the plate was centrifuged at 3000 rpm for 10 minutes to pellet the precipitated proteins, and the resultant supernatants were transferred to a fresh 96-well plate for extraction and analysis.

Samples were analyzed for acetaminophen and acetaminophen-d4 concentrations, using a method that employs HPLC and MS/MS detection; results are shown in FIG. 4.

Summary of Results

Figure 4A:
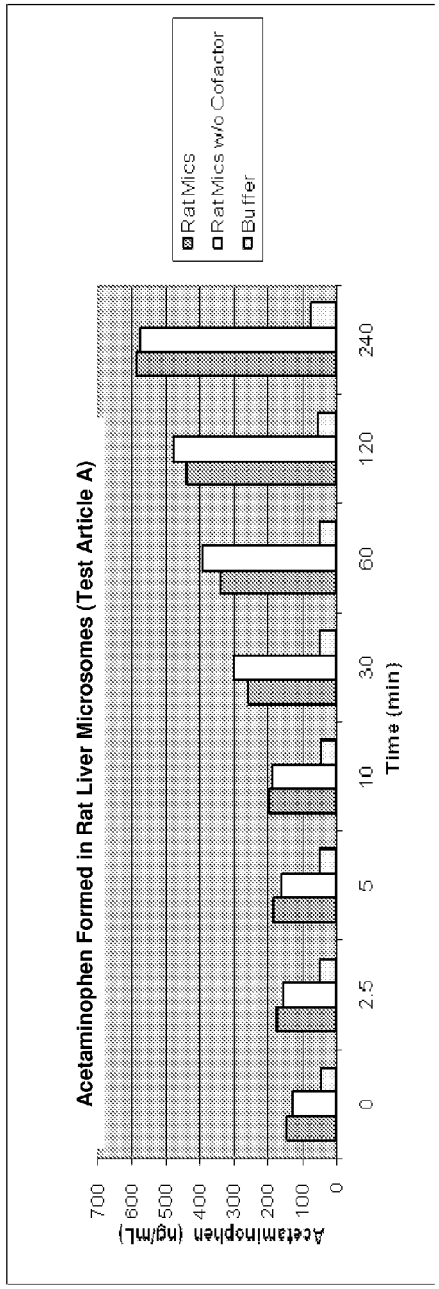
FIG. 4A illustrates acetaminophen concentration (μg/mL) with time following rat liver microsome-mediated metabolism of Test Article A, with and without Cofactor. Acetaminophen concentration (μg/mL) with time following incubation of Test Article A in buffer is also provided.

Test Article A: As illustrated in FIG. 4A, rat microsomes with and without cofactor appear to form acetaminophen at nearly the same rate, and at a level much greater than incubations with buffer. Without being bound by theory, it appears that Test Article A is being converted to acetaminophen by enzymes other than those in the P450 group.

Figure 4B:
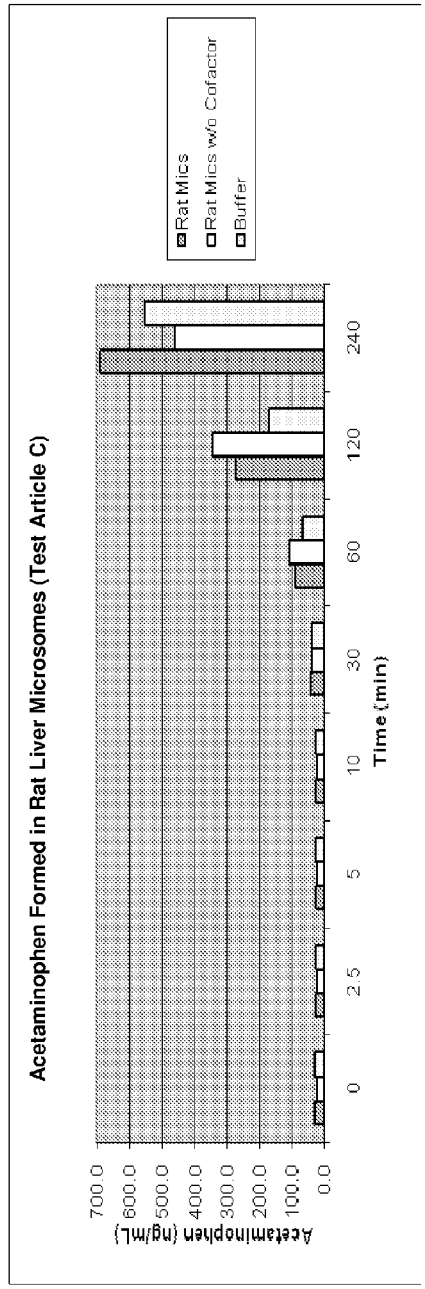
FIG. 4B illustrates acetaminophen concentration (μg/mL) with time following rat liver microsome-mediated metabolism of Test Article C, with and without Cofactor. Acetaminophen concentration (μg/mL) with time following incubation of Test Article C in buffer is also provided.
Figure 4C:
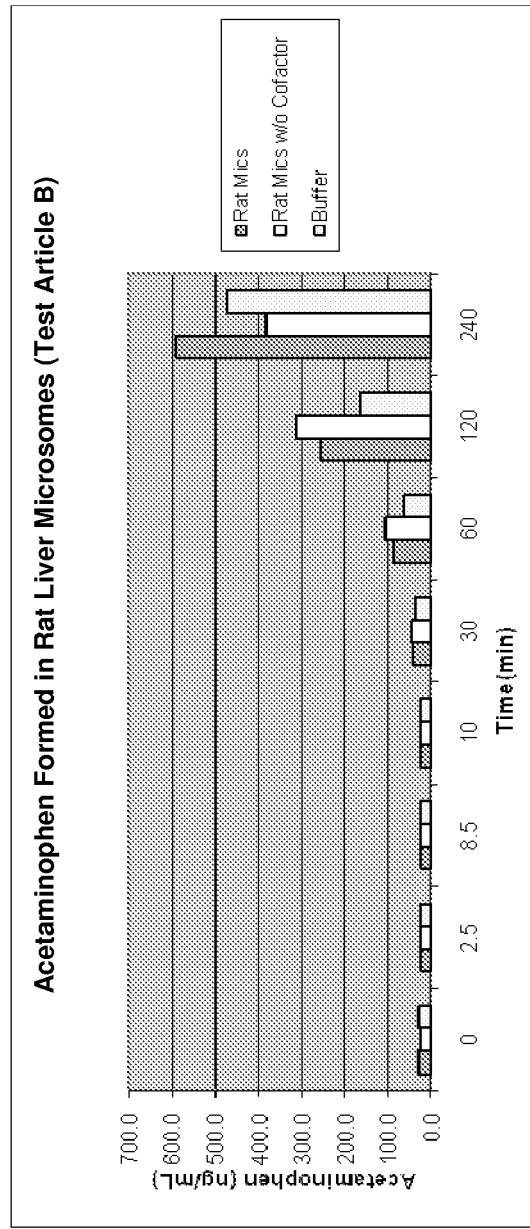
FIG. 4C illustrates acetaminophen concentration (μg/mL) with time following rat liver microsome-mediated metabolism of Test Article B, with and without Cofactor. Acetaminophen concentration (μg/mL) with time following incubation of Test Article B in buffer is also provided.

Test Article B: As illustrated in FIG. 4C, very little conversion to acetaminophen is observed until after 30 minutes. Conversion was observed in all incubation types. Slightly more conversion is observed in the incubations with enzymes than with buffer, but it does not appear that P450 enzymes are responsible for the conversion. Test Article B is not stable in buffer at 37° C.

Test Article C: As illustrated in FIG. 4B, very little conversion to acetaminophen is observed until after 30 minutes. Conversion was observed in all incubation types. Slightly more conversion is observed in the incubations with enzymes than with buffer, but it does not appear that P450 enzymes are responsible for the conversion. Test Article C is not stable in buffer at 37° C.

These date show that Test Article A is the best substrate for metabolism by rat hepatocytes, which is predictive that this compound will be metabolized to release acetaminophen in a similar fashion by other species. Test Article A outperforms Test Articles B and C in this respect. Test Article A is stable in buffer and is thus potentially amenable for development as a stable premixed injection solution.

Example 16

Human Liver Microsome-Mediated Metabolism

The appearance of acetaminophen (APAP) when Test Articles A, B or C are incubated in human liver microsomes at 37° C. was determined. Loss of APAP-d4 was also monitored.

Sample Preparation

One lot consisted of ~150 human mixed gender liver microsomes was purchased from BD Biosciences and stored frozen at −80° C. until use. Compounds were weighed immediately prior use. Test Article A, Test Article B, and Test Article C were weighed on a microbalance and dissolved in water to generate individual stock solutions, each at a concentration of 3.31 mM. Purity was taken into account for each stock solution prepared. APAP-d4 was weighed on a microbalance and dissolved in water to generate a stock solution at a 3.31 mM concentration. Purity was taken into account for the stock preparation.

One part Test Articles A, B or C and one part APAP-d4 was added to three parts water to arrive at an intermediate solution consisting of 662 µM for each compound.

Incubation and Sampling

The intermediate solutions prepared above were added to phosphate buffer to arrive at solutions consisting of 8.827 µM of each compound; these were called Substrate solutions. Incubation wells were placed in a wet ice-bath. 750 µL of Substrate solution was added to the appropriate wells. 750 µL of 100 mM Potassium phosphate was added to wells that did not get Substrate solution. 50 µL of Microsomal suspension (20 mg/mL) was added to the appropriate wells. 50 µL of 100 mM Potassium phosphate buffer, pH 7.4 was added to the appropriate wells that did not receive microsomes. Samples were pre-incubated by shaking at 37° C. for 5 minutes. Just prior to starting the reactions in the next step 80 µL aliquots were removed and "killed" with 200 µL of Stop solution; these were the 0 min samples.

Reactions for the remaining samples were started by adding 180 µL Cofactor Solution (5×) to the appropriate wells. A 180 µL aliquot of 2% sodium bicarbonate in purified water was added to the incubation samples that did not receive cofactor. A 20 µL aliquot of Cofactor Solution (5×) was added to the stopped 0 min samples. A 20 µL aliquot of 2% sodium bicarbonate in purified water was added to the stopped 0 min samples that did not receive cofactor. At 2.5, 5, 10, 30, 60, 120, and 240 minutes, 100 µL of the specified incubation sample was removed and "killed" with 200 µL of Stop Solution. Once all required samples were collected, the plate was centrifuged at 3000 rpm for 10 minutes to pellet the precipitated proteins, and the resultant supernatants were transferred to a fresh 96-well plate for extraction and analysis.

Figure 5A:
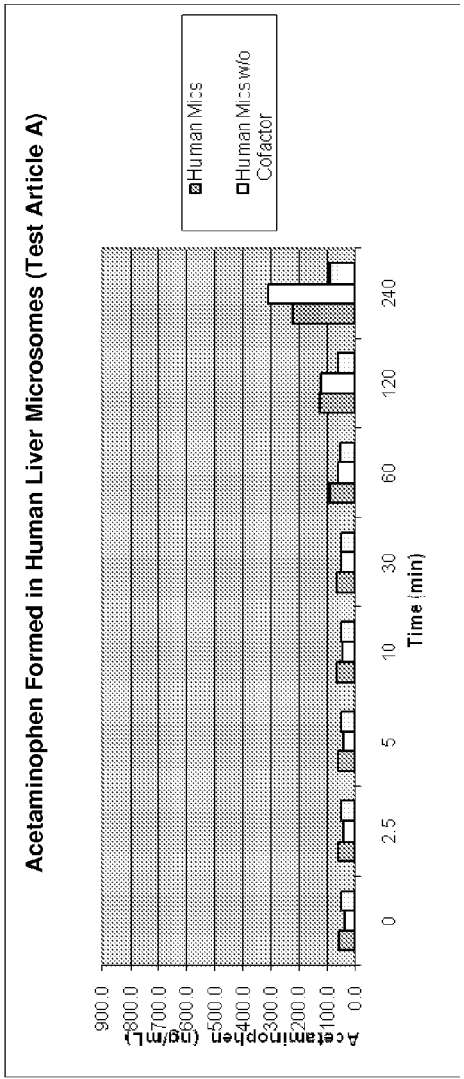
FIG. 5A illustrates acetaminophen concentration (μg/mL) with time following human liver microsome-mediated metabolism of Test Article A, with and without Cofactor. Acetaminophen concentration (μg/mL) with time following incubation of Test Article A in buffer is also provided
Figure 5B:
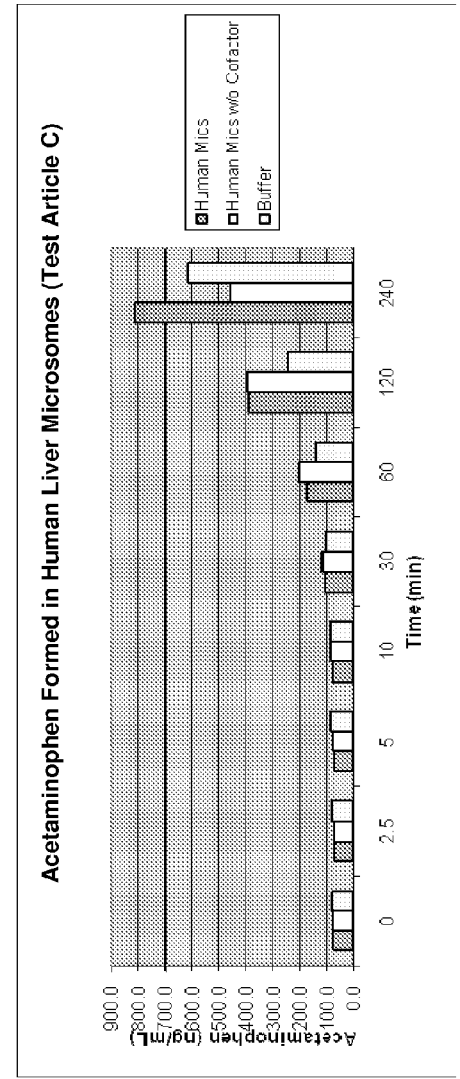
FIG. 5B illustrates acetaminophen concentration (μg/mL) with time following human liver microsome-mediated metabolism of Test Article C, with and without Cofactor. Acetaminophen concentration (μg/mL) with time following incubation of Test Article C in buffer is also provided
Figure 5C:
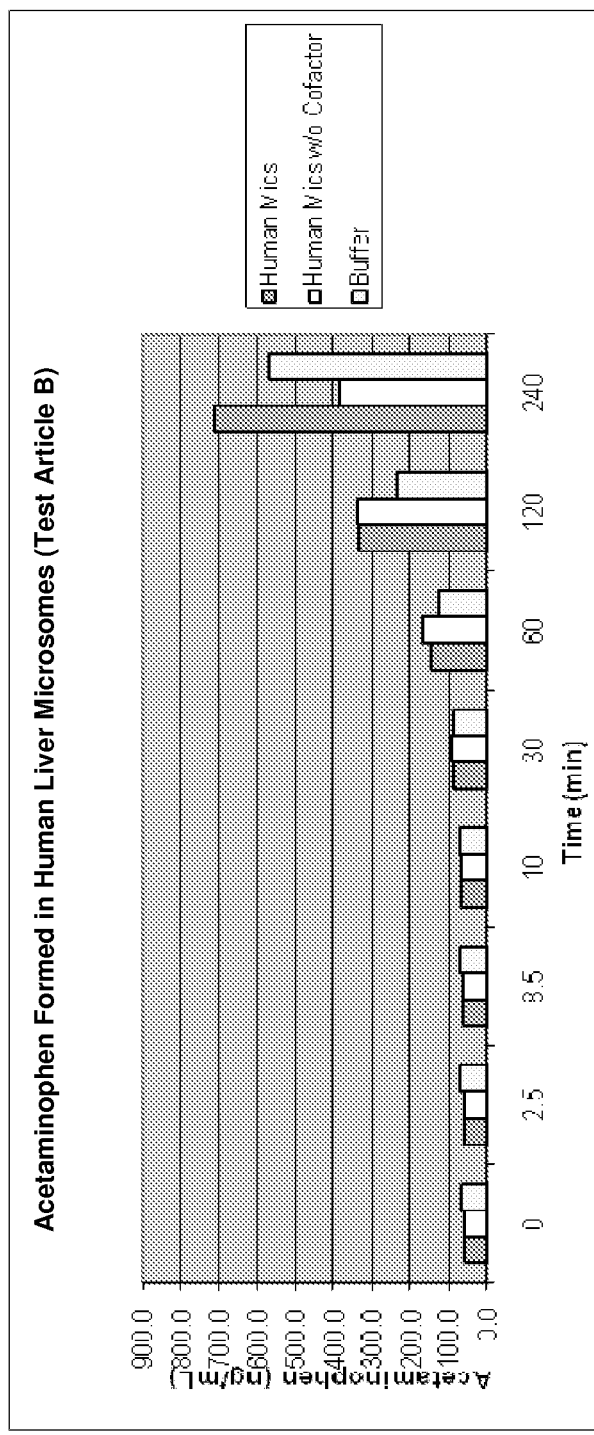
FIG. 5C illustrates acetaminophen concentration (μg/mL) with time following human liver microsome-mediated metabolism of Test Article B, with and without Cofactor. Acetaminophen concentration (μg/mL) with time following incubation of Test Article B in buffer is also provided.

Samples were analyzed for acetaminophen and acetaminophen-d4 concentrations, using a method that employs HPLC and MS/MS detection. Results are shown in FIG. 5.

Summary of Results

For test Article A, human microsomes with and without cofactor appear to form acetaminophen at nearly the same rate, and at a level greater than incubations with buffer. Without being bound by theory, it appears that Test Article A is being converted to acetaminophen by enzymes other than those in the P450 group.

For test Article B, very little conversion to acetaminophen is only observed until after 30 minutes and conversion was observed in all incubation types. Slightly more conversion is observed in the incubations with enzymes than with buffer, but it does not appear that P450 enzymes are responsible for the conversion. Test Article B is not stable in buffer at 37° C.

For test Article C, very little conversion to acetaminophen is observed only until after 30 minutes and conversion was observed in all incubation types. Slightly more conversion is observed in the incubations with enzymes than with buffer, but it does not appear that P450 enzymes are responsible for the conversion. Test Article C is not stable in buffer at 37° C.

These data, as was indicated above for the rat microsome experiments, show that Test Article A is the best substrate for metabolism by human hepatocytes, which is predictive that this compound will be metabolized to release acetaminophen in a similar fashion by humans. Test Article A outperforms Test Articles B and C in this respect. Test Article A is stable in buffer and is thus potentially amenable for development as a stable premixed injection solution.

Example 17A

Test Article A Solubility

Solubility Protocol 10-60 mg of Test Article A was weighed into a 1 mL micro centrifuge tube. 100 µL of solvent was added. Samples were mixed using a vortex mixer, and then sonicated for 15 minutes at ambient temperature. In the event of complete dissolution, more solute was added. The resultant suspensions were centrifuged to yield an off-white saturated solution. A small aliquot of the supernatant was diluted prior to analysis by HPLC. The solubility of Test Article A was determined and results are reported in Table 1.

TABLE 1

Solubility Testing of Test Article A

| Experiment | Solvent System | Sample Area | Mean | Sample Concen. (µg/mL) | Dilution Factor | Solubility (mg/mL) | Temperature ° C. |
|---|---|---|---|---|---|---|---|
| Std: 111 µg/mL | | 86.1 86.1 | 86.15 | 111 | | | |
| 1 | Water | 86.9 86.9 | 86.9 | 112 | 2500 | 280 | 18 |
| 2 | Ethanol | 5.3 5.3 | 5.3 | 7 | 200 | 1 | 18 |
| 3 | 50% Water, Ethanol | 77.4 77.3 | 77.35 | 100 | 2000 | 199 | 18 |
| 4 | PBS | 95.3 95.3 | 95.3 | 123 | 2000 | 246 | 18 |
| Std: 111 µg/mL | | 86.2 86.2 | | | | | |

In the procedure set forth above, it was noted that the concentrated samples became hazy on standing. This was attributed to the samples being inadvertently heated during sonication and centrifugation, and was suspected to cause falsely high results. Samples were therefore equilibrated in a water bath before and after centrifugation as detailed in Example 17B below.

Example 17B

Test Article A Solubility Determined Via Modified Protocol 10-60 mg of Test Article A was weighed into a 1 mL micro centrifuge tube. 100 µL of solvent was added. Samples were mixed using a vortex mixer, and then sonicated for 15 minutes at ambient temperature. In the event of complete dissolution, more solute was added. The resultant suspensions were equilibrated in a water bath for 20 minutes and were centrifuged for 1 minute to yield an off-white saturated solution. The samples were then equilibrated a further 20 minutes in the water bath. 5-10 µL aliquots of the supernatant were diluted into 25 mL of mobile phase using volumetric flasks, prior to analysis by HPLC. The solubility of Test Article A was determined and results are reported in Table 2.

TABLE 2

Solubility Values for Test Article A

| Experiment | Solvent System | Sample Area | Mean | Sample Concen. (µg/mL) | Dilution Factor | Solubility (mg/mL) | Temperature ° C. |
|---|---|---|---|---|---|---|---|
| Std: 111 µg/mL | | 87.8 87.9 | 87.8 | 111 | | | |
| 5 | Propylene Glycol/Water | 58.4 58.6 | 58.5 | 74 | 2500 | 185 | 19 |
| 6 | PEG-400 | 32.6 32.6 | 32.6 | 41 | 2500 | 103 | 19 |
| 7 | PEG-400/Water | 97.0 96.9 | 97.0 | 123 | 2500 | 306 | 19 |
| 8 | pH 5 Buffer | 71.4 71.4 | 71.4 | 90 | 2500 | 226 | 19 |
| 9 | pH 6.5 Buffer | 66.5 66.5 | 66.5 | 84 | 2500 | 198 | 19 |
| 10 | pH 8 Buffer | 62.6 62.6 | 62.6 | 79 | 2500 | 198 | 19 |
| 11 | Propylene Glycol | 21.9 21.9 | 21.9 | 28 | 2500 | 69 | 19 |
| 12 | Water Repeat | 72.8 72.8 | 72.8 | 92 | 2500 | 230 | 19 |
| 13 | pH 6.5 Buffer 35° C. | 64.1 64.2 | 64.2 | 81 | 5000 | 406 | 35 |
| 14 | Water (in Fridge) | 24.8 24.8 | 24.8 | 31 | 2500 | 78 | 0 to 4 |
| Std: 111 µg/mL | | 87.6 87.7 | | | | | |

HPLC Method Used for Sample Analysis:

A HPLC method was developed to quantify Test Article A concentration via external standard analysis, and also monitor and quantify the hydrolysis product APAP. Linearity was determined over the range 20 to 120 µg/mL, and reproducibility was determined at 100 µg/mL.

| Conditions | |
|---|---|
| Column | Synergi-POLAR 150 mm × 4.6 mm, 4 µm (Phenomenex) |
| Mobile Phase | 20 mM Potassium Dihydrogen Phosphate, 10 mM Dipotassium Hydrogen Phosphate, Acetonitrile (42.5:42.5:15) isocratic |
| Flow Rate | 1.0 mL/min |

-continued

| Conditions | |
|---|---|
| Detection | UV at 244 nm, 1AUFS |
| Sample Prep | Dissolve in mobile phase or PBS, dilute to ~100 µg/mL |
| Injection | 20 µL by autosampler |
| Run Time | 8 min |
| Retention times | APAP: 3.8-4.5 min |
| | Test Article A: 5.3-6.3 min |

Buffer Recipe: Potassium Dihydrogen Phosphate: 1.16 g; Dipotassium Hydrogen Phosphate: 0.74 g; HPLC Water 850 mL; Acetonitrile (HPLC): 150 mL. Ingredients were combined and stirred to dissolve and degassed thoroughly prior to use.

Results Summary

The solubility of Test Article A in various solvents and at different temperatures was assessed as noted above. The results are reported in Table 3 in order of descending solubility.

TABLE 3

Summary of Solubility Data for Test Article A

| Solvent | Temperature (° C.) | Solubility (mg/mL) | Note |
|---|---|---|---|
| pH 6.5 Buffer | 35 | 406 | |
| PEG-400, 50% Water | 19 | 306 | |
| Water | 19 | 230 | 1, 2 |
| pH 5 Buffer | 19 | 226 | |
| pH 6.5 Buffer | 19 | 210 | |
| Ethanol, 50% Water | 18 | 199 | 3 |
| pH 8 Buffer | 19 | 198 | |
| Propylene Glycol, 50% Water | 19 | 185 | |
| PEG-400 | 19 | 103 | |
| Water | 4 | 78 | |
| Propylene Glycol | 19 | 69 | |
| Ethanol | 18 | 1 | |

Table 1 Notes:
1. As indicated above, early results indicated a higher result, but samples became hazy on standing due to poor temperature control. The method was amended and the sample repeated.
2. Result confirmed using a second batch of material.
3. Result may be high due to poor temperature control.

The above results indicate that Test Article A has exceptional solubility in solutions which approximate the characteristics of blood (best exemplified by the 406 mg/mL value at pH 6.5 buffer at 37° C.). Hence, once injected into the human bloodstream, it is unlikely that this compound would show significant crystallization at the injection site, but rather be distributed throughout the vasculature. It is well known in the field of parenteral formulation development that crystal formation at the injection site is responsible for most adverse effects of test compounds. See, Johnson J L, He Y, Yalkowsky S H. Prediction of precipitation-induced phlebitis: a statistical validation of an in vitro model. J Pharm Sci. 2003 August; 92(8):1574-81. The high solubility (306 mg/mL) displayed in a solvent system (50% PEG-400 and 50% water) which could be the basis for a parenteral formulation suggests that a very high-concentration, low-dose-volume formulation may be developed. Currently, acetaminophen is administered via a formulation which has a concentration of 10 mg/mL, and thus requires a 100 mL infusion to deliver the therapeutic dose of 1000 mg.

Example 18

Test Article B, C and Acetaminophen Solubility

Using the same experimental protocol as described in Example 17, Test Articles B and C were found to have a very high solubility in phosphate-buffered saline (pH 7.2) at room temperature. The solubility data for acetaminophen are quite consistent with literature values, and show that Test Articles A, B and C could have up to about 30-fold high aqueous solubility than acetaminophen.

| | Mean | Sample Area | Mean | Sample Concen. (µg/mL) | Solubility (mg/mL) |
|---|---|---|---|---|---|
| Test Article B Solubility Study (Room Temperature) | | | | | |
| Standard Area (103 µg/mL) | | | | | |
| | 54.9 | | 45.3 | | |
| | 54.9 | 54.9 | 45.2 | 45.3 | 84.9 | 424.5 |
| Test Article C Solubility Study (Room Temperature) | | | | | |
| Standard Area (107 µg/mL) | | | | | |
| | 56.2 | | 49.5 | | |
| | 56.3 | 56.3 | 53.9 | 51.7 | 98.3 | 491.7 |
| Acetaminophen Room Temperature Solubility Study (Aldrich Lot 05615EE) | | | | | |
| Standard Area (95.2 µg/mL) | | | | | |
| | 104.1 | | 71.6 | | |
| | 104.1 | 104.1 | 71.7 | 71.7 | 65.5 | 13.1 |

These data show that Test Articles B and C have even higher aqueous solubility than Test Article A, which predicts that both B and C would also be attractive candidates for development as high-concentration, low-dose-volume formulations. These results illustrate that the Test Articles are much more water soluble than acetaminophen (about 30-fold higher), meaning they have the potential to be formulated for bolus intravenous or parenteral administration.

What is claimed:

1. A compound of the formula (I):

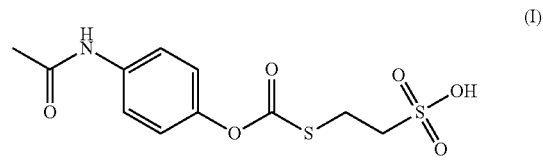 [SMILES: CC(=O)Nc1ccc(OC(=O)SCCS(=O)(=O)O)cc1]

or a pharmaceutically acceptable salt thereof.

2. The compound of claim 1, wherein the compound is a salt of the formula (Ia):

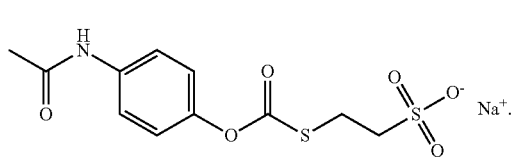

3. A compound of the formula (II):

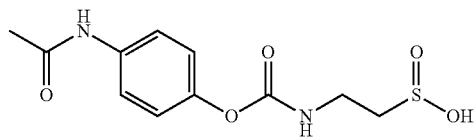 [SMILES: CC(=O)Nc1ccc(OC(=O)NCCS(=O)O)cc1]

or a pharmaceutically acceptable salt thereof.

4. The compound of claim 3 wherein the compound is a salt of the formula (IIa):

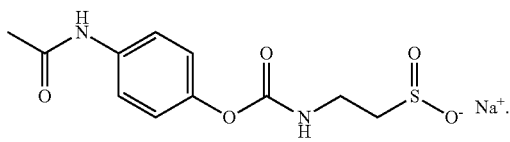

5. A formulation comprising a compound of claim 1 or 3 and a pharmaceutically acceptable carrier.

6. The formulation of claim 5, wherein the pharmaceutically acceptable carrier comprises saline.

7. A method of treating a disease or condition selected from the group consisting of pain, fever, inflammation, ischemic injury, and neuronal injury, comprising administering to an individual in need thereof an effective amount of a compound according to claim 1 or 3.

8. The method of claim 7, wherein the compound is administered parenterally.

9. A kit for the treatment or prevention of a disease or condition selected from the group consisting of pain, fever, inflammation, ischemic injury, and neuronal injury, comprising a compound of claim 1 or 3, or a pharmaceutically acceptable salt thereof and instructions for use.

* * * * *